(12) United States Patent
Conger et al.

(10) Patent No.: US 7,916,947 B2
(45) Date of Patent: Mar. 29, 2011

(54) FALSE ALARM RECOGNITION IN HYPERSPECTRAL GAS PLUME IDENTIFICATION

(75) Inventors: James L. Conger, San Ramon, CA (US); Janice K. Lawson, Tracy, CA (US); William D. Aimonetti, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 12/496,476

(22) Filed: Jul. 1, 2009

(65) Prior Publication Data

US 2011/0002546 A1      Jan. 6, 2011

(51) Int. Cl.
*G06K 9/00* (2006.01)
(52) U.S. Cl. ........ 382/181; 382/100; 382/103; 382/191; 356/432; 356/437; 250/338.5; 250/339.11
(58) Field of Classification Search .................. 382/100, 382/103, 181, 191; 356/432, 437; 250/338.5, 250/339.11
See application file for complete search history.

(56) References Cited

U.S. PATENT DOCUMENTS

| | | | | |
|---|---|---|---|---|
| 5,430,293 | A * | 7/1995 | Sato et al. | 250/330 |
| 6,664,533 | B1 * | 12/2003 | van der Laan et al. | 250/222.2 |
| 6,750,453 | B1 * | 6/2004 | Nelson et al. | 250/338.5 |
| 6,822,742 | B1 * | 11/2004 | Kalayeh et al. | 356/437 |
| 7,075,653 | B1 * | 7/2006 | Rutherford | 356/437 |
| 7,649,174 | B2 * | 1/2010 | Mammen et al. | 250/330 |
| 7,675,616 | B1 * | 3/2010 | Carney et al. | 356/326 |
| 7,705,988 | B2 * | 4/2010 | Richman | 356/437 |
| 7,710,568 | B1 * | 5/2010 | Paige et al. | 356/437 |

OTHER PUBLICATIONS

Broadwater, Joshua B. et al., "Detection of gas plumes in cluttered environments using long-wave infrared hyperspectral sensors" Proc. of SPIE vol. 6954 69540R-1, 2008.
Manolakis, D. et al., "Software Algorithms for False Alarm Reduction in LWIR Hyperspectral Chemical Agent Detection" Proc. of SPIE vol. 6966 69661U-1, 2008.
Theiler, James et al., "Characterizing non-Gaussian clutter and detecting weak gaseous plumes in hyperspectral imagery" Proc. of SPIE vol. 5806, 2005, pp. 182-193.
Vallières, Alexandre et al., "Algorithms for Chemical Detection, Identification and Quantification for Thermal Hyperspectral Imagers" Proc. of SPIE vol. 5995 59950G-1, 2005.

* cited by examiner

*Primary Examiner* — Bhavesh M Mehta
*Assistant Examiner* — Stephen R Koziol
(74) *Attorney, Agent, or Firm* — Eddie E. Scott; James S. Tak

(57) ABSTRACT

According to one embodiment, a method for analyzing hyperspectral data includes collecting first hyperspectral data of a scene using a hyperspectral imager during a no-gas period and analyzing the first hyperspectral data using one or more gas plume detection logics. The gas plume detection logic is executed using a low detection threshold, and detects each occurrence of an observed hyperspectral signature. The method also includes generating a histogram for all occurrences of each observed hyperspectral signature which is detected using the gas plume detection logic, and determining a probability of false alarm (PFA) for all occurrences of each observed hyperspectral signature based on the histogram. Possibly at some other time, the method includes collecting second hyperspectral data, and analyzing the second hyperspectral data using the one or more gas plume detection logics and the PFA to determine if any gas is present. Other systems and methods are also included.

19 Claims, 15 Drawing Sheets

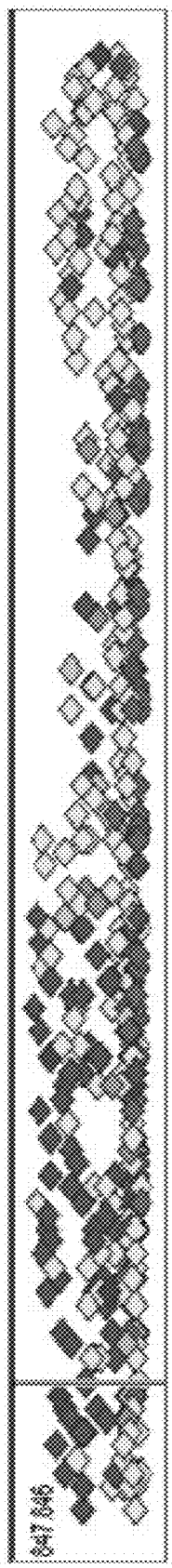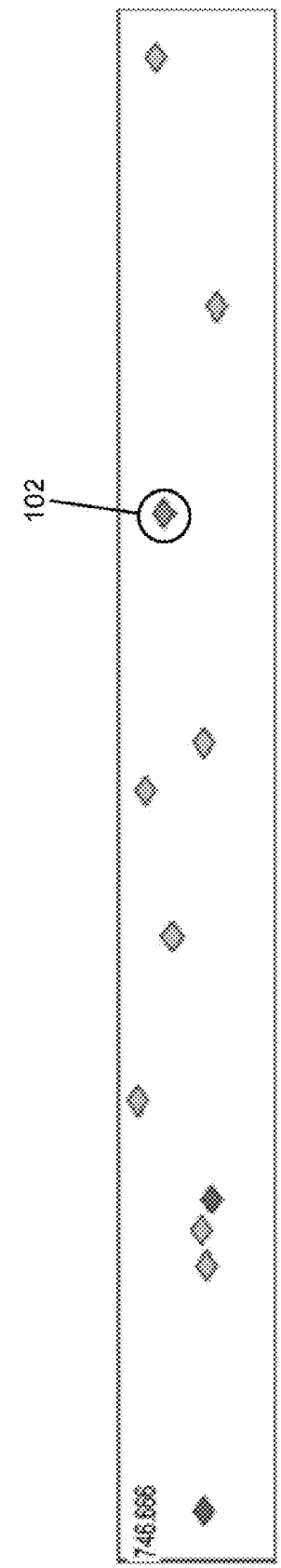
FIG. 1A
FIG. 1B

FALSE ALARM RECOGNITION IN HYPERSPECTRAL GAS PLUME IDENTIFICATION

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to hyperspectral gas plume analysis, and more particularly, to systems and methods for recognizing false alarms in hyperspectral gas plume identification.

BACKGROUND

Long wave infrared (LWIR) hyperspectral imaging data can be used for gas plume identification. This technology, although incredibly useful for identifying gas plumes without taking direct measurements from the source area, has a few problems associated with the efficient use of the technology. One of these problems is false gas identifications that may occur when the hyperspectral data is analyzed to identify chemical gas plumes.

Generally, a library of hyperspectral gas data signatures is used to compare against an observed hyperspectral gas data signature based on an analysis logic. If the observed hyperspectral gas data signature compares favorably to at least one of the library of hyperspectral gas data signatures, then the logic indicates that this particular gas is present near the source area where the hyperspectral data was collected. However, many items may cause a hyperspectral data signature which may be similar enough to a gas' hyperspectral data signature to appear to be that gas, when in fact it is not that gas. When these items are falsely identified as a gas, they are typically called 'false alarms' or 'false hits.' When a gas is properly identified by analysis of the hyperspectral data, it may trigger an alarm. Generally, each alarm is reviewed by someone to determine if it is a 'false alarm' or is actually a gas present in the source area. There is a tremendous amount of manual workload that is performed in order to pick through the results of thousands of hyperspectral data sets and to eliminate likely false alarms from the data.

Therefore, it would be very beneficial to have an automated method of eliminating or greatly reducing the amount of false alarms that are indicated through hyperspectral data analysis to increase the efficiency and ease of use of hyperspectral data analysis to identify gas plumes.

SUMMARY

According to one embodiment, a method for analyzing hyperspectral data includes collecting a first plurality of hyperspectral data sets of a scene using a hyperspectral imager during a period where no gas is expected to be present in the scene and analyzing the first plurality of hyperspectral data sets using at least one gas plume detection logic. The at least one gas plume detection logic is executed using a low detection threshold, and detects each occurrence of an observed hyperspectral signature. The method also includes generating a histogram for all occurrences of each observed hyperspectral signature which is detected using the at least one gas plume detection logic, and determining a probability of false alarm (PFA) for all occurrences of each observed hyperspectral signature based on the histogram. Further, the method includes, possibly at a later time, collecting a second plurality of hyperspectral data sets of the scene using the hyperspectral imager, and analyzing the second plurality of hyperspectral data sets using the at least one gas plume detection logic and the probability of false alarm (PFA) to determine if any gas is present in the scene.

According to another embodiment, a system for detecting gas plumes includes a processor and a memory operatively coupled to the processor. The processor receives a first plurality of hyperspectral data sets of a scene collected by a hyperspectral imager during a period where no gas is expected to be present in the scene and analyzes the first plurality of hyperspectral data sets using at least one gas plume detection logic which is executed using a low detection threshold. The at least one gas plume detection logic detects each occurrence of an observed hyperspectral signature. Also, the processor generates a histogram for all occurrences of each observed hyperspectral signature which is detected using the at least one gas plume detection logic, and determines a probability of false alarm (PFA) for all occurrences of each observed hyperspectral signature based on the histogram. Possibly at a later time, the processor receives a second plurality of hyperspectral data sets of the scene using the hyperspectral imager, and analyzes the second plurality of hyperspectral data sets using the at least one gas plume detection logic and the probability of false alarm (PFA) to determine if any gas is present in the scene.

In another embodiment, a computer program product embodied on a computer readable medium includes computer readable code. The computer readable code is configured for receiving a first plurality of hyperspectral data sets of a scene from a hyperspectral imager collected during a period where no gas is expected to be present in the scene, and for analyzing the first plurality of hyperspectral data sets using at least one gas plume detection logic. The at least one gas plume detection logic is executed using a low detection threshold and detects each occurrence of an observed hyperspectral signature. Also, the computer readable code is configured for generating a histogram for all occurrences of each observed hyperspectral signature which is detected using the at least one gas plume detection logic, and for determining a probability of false alarm (PFA) for all occurrences of each observed hyperspectral signature based on the histogram. The computer readable code is also configured for receiving a second plurality of hyperspectral data sets of the scene from the hyperspectral imager possibly at a later time, and for analyzing the second plurality of hyperspectral data sets using the at least one gas plume detection logic and the probability of false alarm (PFA) to determine if any gas is present in the scene.

In another embodiment, a method for analyzing hyperspectral data includes collecting a first plurality of hyperspectral data sets of a scene using a hyperspectral imager during a period where no gas is expected to be present in the scene, and analyzing the first plurality of hyperspectral data sets using at least one gas plume detection logic. The at least one gas plume detection logic is executed using a low detection threshold, and detects each occurrence of an observed hyperspectral signature. Also, the method includes comparing an observed hyperspectral signature from the plurality of first hyperspectral data sets to a library of known hyperspectral gas signatures, calculating a goodness-of-fit statistic for the each occurrence of an observed hyperspectral signature against a signature of a known gas type from the library of known hyperspectral gas signatures, generating a histogram for all occurrences of each observed hyperspectral signature which is detected using the at least one gas plume detection logic, and determining a probability of false alarm (PFA) for all occurrences of each observed hyperspectral signature based on the histogram. Possibly at a later time, the method includes collecting a second plurality of hyperspectral data sets of the scene using the hyperspectral imager, and analyzing the second plurality of hyperspectral data sets. Analyzing the second plurality of hyperspectral data sets includes detecting each occurrence of an observed hyperspectral signature in the second plurality of hyperspectral data sets, calculating a goodness-of-fit statistic for each occurrence of an observed hyperspectral signature from the second plurality of hyperspectral data sets against a signature of a known gas type from the library of known hyperspectral signatures, determining a probability of false alarm (PFA) at the goodness-of-fit statistic for the observed hyperspectral signature from the corresponding histogram, outputting a false alarm if the probability of false alarm (PFA) is equal to or above a preset threshold, and outputting an occurrence of the known gas type if the probability of false alarm (PFA) is below the preset threshold.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 1A is a schematic diagram of exploitation results before filtering according to one embodiment.

FIG. 1B is a schematic diagram of exploitation results after filtering is applied according to one embodiment.

FIG. 48 shows a spectral fit for false alarm number 2 in FIG. 3.

DETAILED DESCRIPTION

Figure 2:
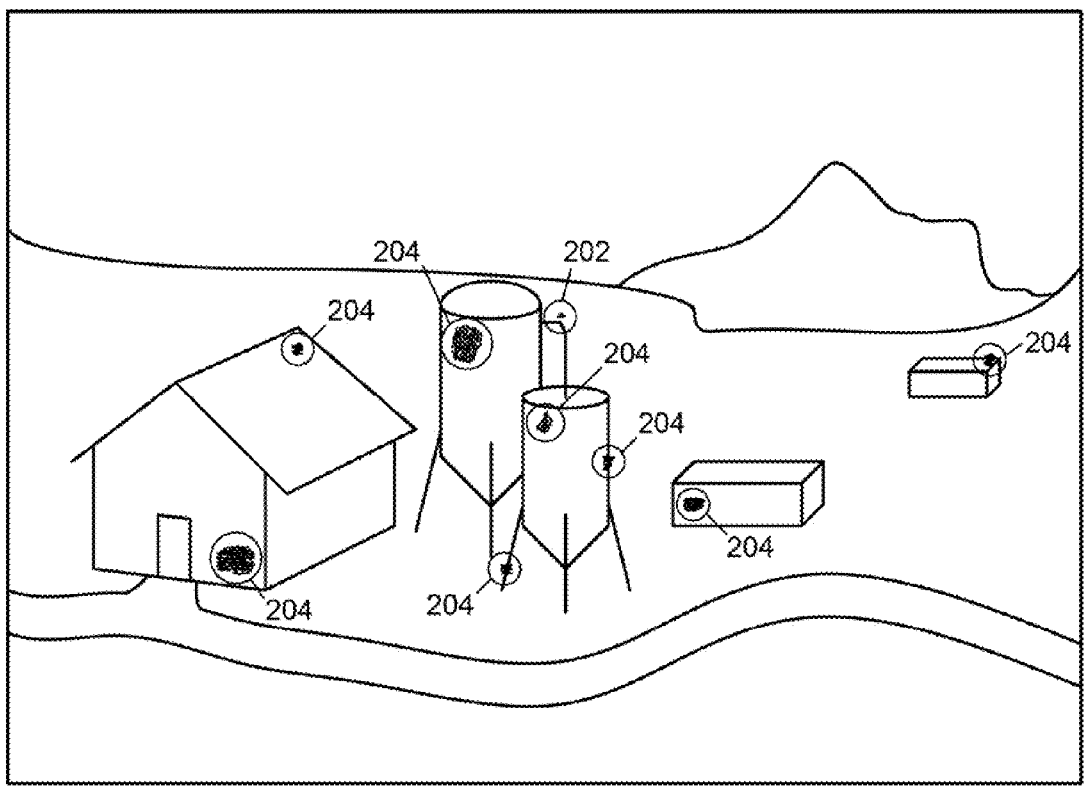
FIG. 2 shows a simplified rendering of a hyperspectral image which is consistent with images produced from data collected over a period of days.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

According to some embodiments, statistical evaluation of false alarms allows for automation of the detection of likely false alarms in situations where a target is being observed on more than one occasion. Automation of the detection of likely false alarms may be used to reduce the time, cost, and effort of exploiting hyperspectral data, and/or as a method for increasing sensitivity to identifying gases at low gas rates. The benefits of statistical filtering depend on the conditions, but may result in as much as a five time increase in probability of detection of likely false alarms at a constant false alarm rate.

False alarms are generally not a problem when large amounts of gas are being released, as detection thresholds can be set high enough to suppress false alarms without hiding the strong chemical plume signatures. As the gas rates diminish, false alarms are increasingly problematic, as the gas plume signal is of roughly the same strength as that of the false alarms. For example, a weak gas release in a cluttered environment may appear as a weak signal compared to multiple other false alarm signals which may be created by features in the background rather than by a gas.

The impact of statistical filtering of false alarms can be seen by viewing a timeline of exploitation results from a persistent sensor, e.g., a sensor which collects hyperspectral data at multiple times. FIG. 1A shows the unfiltered results collected over the course of several days for a particular scene. The majority of the entries are false alarms. FIG. 1B shows the same timeline after filtering has been applied. There are two gases present which are easily identified after the false alarm clutter is suppressed.

The data used to formulate the examples included herein has leveraged data obtained with the Denali ground-based hyperspectral imaging (GBHSI) sensor. GBHSI allows for hundreds of experiments to be undertaken at a much lower cost than equivalent airborne data collection. It is anticipated that airborne collection of data will mimic that of data collected using the GBHSI sensor. False alarm filtering is also expected to be important for maximizing the utility of bolometric hyperspectral imaging (HSI) sensors.

In one general embodiment, a method for analyzing hyperspectral data comprises collecting a first plurality of hyperspectral data sets of a scene using a hyperspectral imager during a period where no gas is expected to be present near the scene; analyzing the first plurality of hyperspectral data sets using at least one gas plume detection logic, wherein the at least one gas plume detection logic is executed using a low detection threshold, wherein the at least one gas plume detection logic detects each occurrence of an observed hyperspectral signature; generating a histogram for all occurrences of each observed hyperspectral signature which is detected using the at least one gas plume detection logic; determining a probability of false alarm (PFA) for all occurrences of each observed hyperspectral signature based on the histogram; collecting a second plurality of hyperspectral data sets of the scene using the hyperspectral imager; and analyzing the second plurality of hyperspectral data sets using the at least one gas plume detection logic and the probability of false alarm (PFA) to determine if any gas is present near the scene.

In another general embodiment, a system for detecting gas plumes comprises a processor and a memory operatively coupled to the processor. The processor receives a first plurality of hyperspectral data sets of a scene collected by a hyperspectral imager during a period where no gas is expected to be present near the scene, and analyzes the first plurality of hyperspectral data sets using at least one gas plume detection logic which is executed using a low detection threshold. The at least one gas plume detection logic detects each occurrence of an observed hyperspectral signature. The processor also generates a histogram for all occurrences of each observed hyperspectral signature which is detected using the at least one gas plume detection logic, determines a probability of false alarm (PFA) for all occurrences of each observed hyperspectral signature based on the histogram, receives a second plurality of hyperspectral data sets of the scene using the hyperspectral imager, and analyzes the second plurality of hyperspectral data sets using the at least one gas plume detection logic and the probability of false alarm (PFA) to determine if any gas is present near the scene.

In yet another general embodiment, a computer program product embodied on a computer readable medium comprises computer readable code. The computer readable code is configured for receiving a first plurality of hyperspectral data sets of a scene from a hyperspectral imager collected during a period where no gas is expected to be present near the scene; for analyzing the first plurality of hyperspectral data sets using at least one gas plume detection logic, wherein the at least one gas plume detection logic is executed using a low detection threshold, wherein the at least one gas plume detection logic detects each occurrence of an observed hyperspectral signature; and for generating a histogram for all occurrences of each observed hyperspectral signature which is detected using the at least one gas plume detection logic. The computer readable code is also configured for determining a probability of false alarm (PFA) for all occurrences of each observed hyperspectral signature based on the histogram; for receiving a second plurality of hyperspectral data sets of the scene from the hyperspectral imager; and for analyzing the second plurality of hyperspectral data sets using the at least one gas plume detection logic and the probability of false alarm (PFA) to determine if any gas is present near the scene.

In another general embodiment, a method for analyzing hyperspectral data comprises collecting a first plurality of hyperspectral data sets of a scene using a hyperspectral imager during a period where no gas is expected to be present near the scene; analyzing the first plurality of hyperspectral data sets using at least one gas plume detection logic, wherein the at least one gas plume detection logic is executed using a low detection threshold, wherein the at least one gas plume detection logic detects each occurrence of an observed hyperspectral signature; comparing an observed hyperspectral signature from the plurality of first hyperspectral data sets to a library of known hyperspectral gas signatures; calculating a goodness-of-fit statistic for the each occurrence of an observed hyperspectral signature against a signature of a known gas type from the library of known hyperspectral gas signatures; generating a histogram for all occurrences of each observed hyperspectral signature which is detected using the at least one gas plume detection logic; and determining a probability of false alarm (PFA) for all occurrences of each observed hyperspectral signature based on the histogram. The method also includes collecting a second plurality of hyperspectral data sets of the scene using the hyperspectral imager; and analyzing the second plurality of hyperspectral data sets, wherein he analyzing comprises detecting each occurrence of an observed hyperspectral signature in the second plurality of hyperspectral data sets; calculating a goodness-of-fit statistic for each occurrence of an observed hyperspectral signature from the second plurality of hyperspectral data sets against a signature of a known gas type from the library of known hyperspectral signatures; determining a probability of false alarm (PFA) at the goodness-of-fit statistic for the observed hyperspectral signature from the corresponding histogram; outputting a false alarm if the probability of false alarm (PFA) is equal to or above a preset threshold; and outputting an occurrence of the known gas type if the probability of false alarm (PFA) is below the preset threshold.

Source of False Alarms

Although there are a number of excellent tools for detecting and identifying chemical gas plumes in LWIR HSI data, all of the tools generate false alarms when observing cluttered scenes (e.g., scenes with multiple features in the background that potentially may cause false alarms). Generally, gas detection works by finding portions of a scene that are spectrally anomalous compared with the background (modeled from scene statistics). If the background is uniform, this approach works very well. If the scene contains spectrally complex materials (clutter), such as manmade objects, the background itself contains anomalies. If large libraries are used to identify gases, some of the background anomalies will inevitably be spectrally similar to chemicals within the spectral window of the instrument. This leads to the algorithm falsely classifying a portion of the background as a chemical gas plume. In other words, the background feature causes a false alarm.

Note: The results discussed herein were processed using standard matched filter detection followed by gas identification using least squares fits in whitened space. The Pacific Northwest National Laboratory (PNNL) Version 11 spectral gas library, containing 498 chemical gases, was used for identification of gases. This or any other spectral gas library could also be used with any of the various embodiments of the invention described herein in order to identify which type of gas is present near the source area.

Examples and Preferred Embodiments

Several of the examples were deliberately structured to show large amounts of clutter. For example, FIG. 2 shows a simplified rendering of a hyperspectral image which is consistent with images produced from data collected over a period of days. The locations of the false alarms are marked as collections of lines forming a darkened area 204, while the single instance where gas is present is marked as 202. Each of these false alarms 204 may be indicating a different type of chemical gas plume, which would normally appear as a separate color on a hyperspectral image. As is often the case, reflective metal surfaces may be strong generators of false alarms 204. This example shows what may have resulted from collecting data at a low threshold to deliberately generate false alarms. At higher thresholds, only the strongest false alarms would remain.

Periods with no gas present near the scene may be used to create a Probability of False Alarm (PFA) map of the scene. This PFA map may display a white-to-black scale such that zero false alarms recorded are indicated as black and 100% false alarms recorded in every scene is indicated as white. Generally, a PFA map will have little to no grey areas, indicating that false alarms are generally stable in location. The same locations tend to generate false alarms consistently.

Since false alarms are generated by spectral anomalies, it is tempting to try a spectral anomaly measurement as a predictor of false alarms. Unfortunately, this approach tends to only work for the strongest anomalies. An RX image may be taken of the same scene from FIG. 2, where the RX is defined as:

$$RX = (s-m)K^{-1}(s-m)$$

where s is the pixel spectrum, m is the mean spectrum for the same spectral hand, and $K^{-1}$ is the inverse of the scene covariance matrix.

RX measures the distance of the pixels spectrum from the mean spectrum, in the whitened space used for detection and identification of gases. There is only a weak relationship between RX and PFA exits. Tests with airborne data have also shown RX to only weakly correlate with PFA. Other spectral anomaly detectors, such as mean spectral variance (unwhitened difference from the mean) also show limited success.

The fundamental problem with an anomaly-only based PFA prediction is that false alarms must pass two filters in the gas exploitation algorithms in order to be detected:

1) The false alarms are a spectral anomaly.
2) The false alarms resemble a chemical in the identification library.

If the false alarms do not adhere to both of these conditions, then they are not predicted to be false alarms by an anomaly-only based PFA prediction.

The second step, spectral identification, is a strong filter and rejects the vast majority of false alarms even in cases where large chemical identification libraries are used. When a spectral feature in the background closely resembles at least one chemical in the library, it is identified as a false alarm. Estimation of PFA may therefore consider the identity of the false alarm, not simply its signal strength, in order to perform better.

Spatial Versus Spectral Filtering

GBHSI sensors typically stare at the same scene for periods of time ranging from minutes, to hours, to months, to even more time. Since the same false alarm locations persist from scene to scene, it is reasonable to consider simply masking off areas of the image that are problematic (e.g., include consistent false alarms) and only dealing with the remainder of the scene. This approach works well in many cases, but has certain disadvantages:

1. The spatial approach is difficult to apply to the more general problem of false alarms seen by a moving sensor, such as an airborne system. Since embodiments may be used for both airborne and ground-based systems, robustness of operation in airborne situations may be a consideration in design. Registration errors, and changes in areas of coverage between scenes make spatial false alarm matching extremely difficult to automate with airborne systems.
2. False alarm regions are often caused by hot surfaces in a scene. These generate false alarms, but also tend to generate the best detections/identifications for gas plumes because they provide a higher thermal contrast between the plume and the background.
3. Masking these hot areas as suspicious ends up eliminating a strong source for gas identifications. A better system that can reject weak false alarms, but accept strong gas signatures from these hot areas would be beneficial.
4. Despite best efforts, GBHSI systems generally seem to be bumped and adjusted in the course of long collects. This can be compensated for by co-registration of successive images, or by constantly updating the spatial false alarm (FA) map, but the benefits of the spatial approach tends to fade in real world application.

Therefore, the remainder of the descriptions included herein concentrate on spectral filtering of false alarms.

False Alarm Identities

False alarms generally do not maintain a constant chemical identity over time, particularly when large chemical identification libraries are used. This effect has been studied by observing the same scene for periods of several days.

Figure 3:
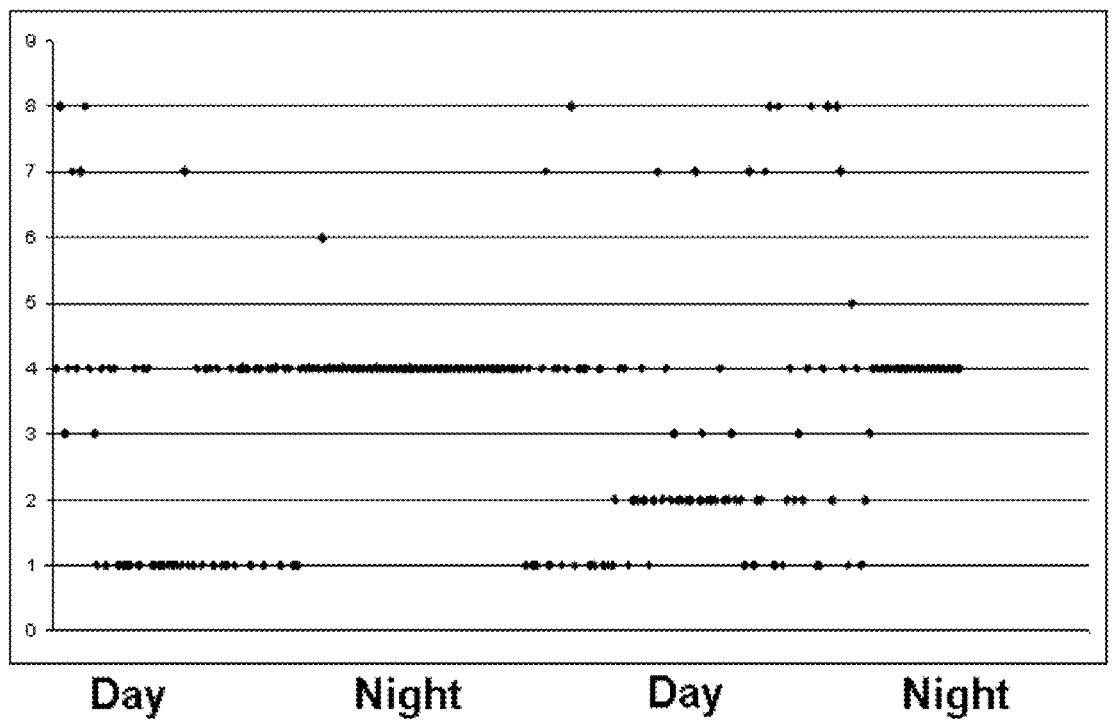
FIG. 3 is a timeline showing eight different chemical identities for one false alarm region.
Figure 4A:
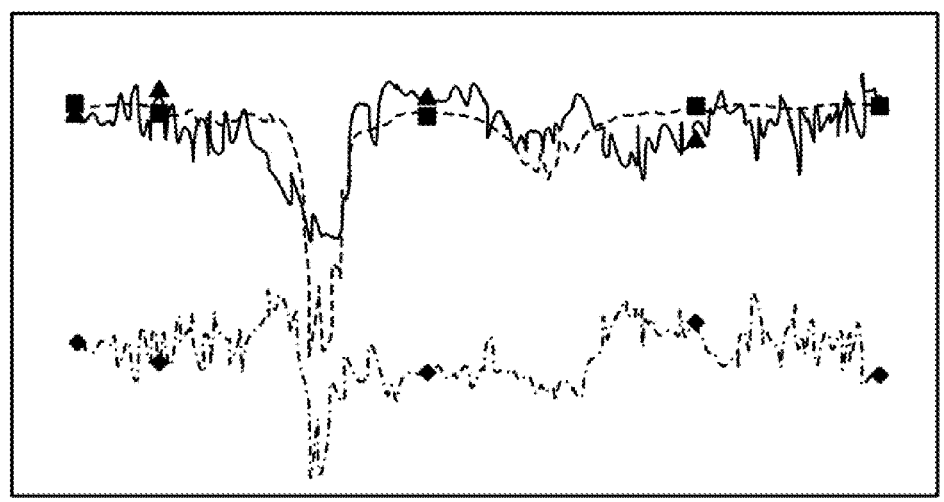
FIG. 4A shows a spectral fit for false alarm number 4 in FIG. 3.
Figure 4B:
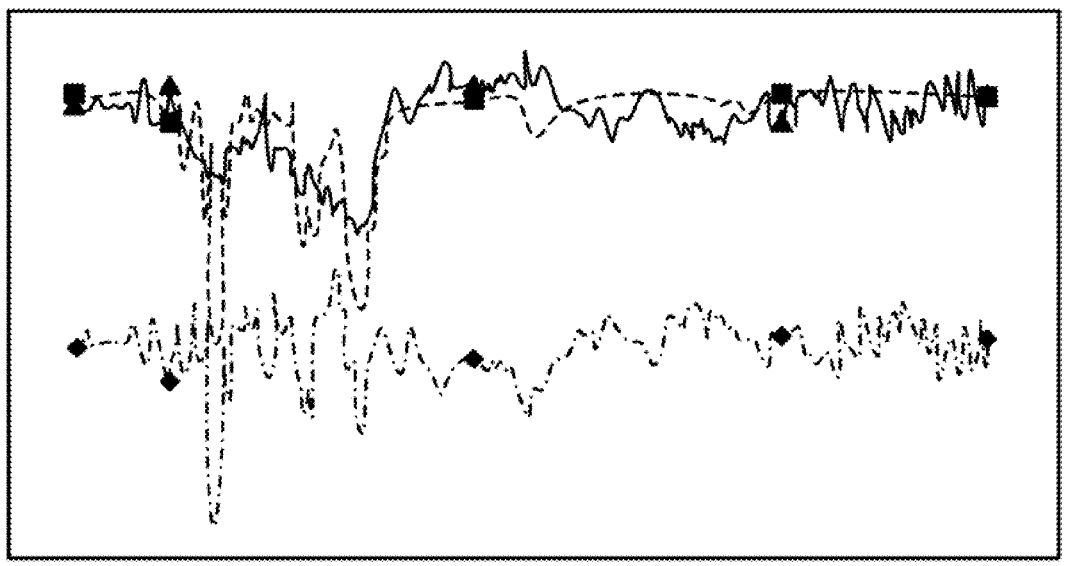
FIG. 4C shows a spectral fit for false alarm number 1 in FIG. 3.
Figure 4C:
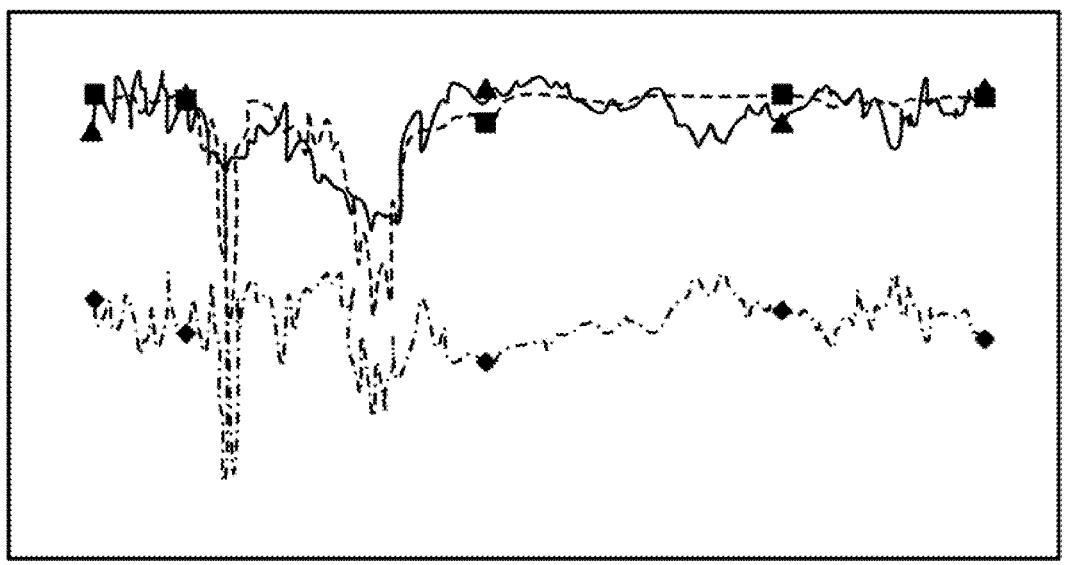

FIG. 3 shows a timeline of the chemical identities for one false alarm producing anomaly observed during data collecting. Each mark on the plot indicates that this chemical (1, 2, ... 8) was falsely identified. Over a period of two days, the same location (anomaly) triggered a continuous false alarm. However, the same location was (falsely) identified as eight different chemicals. Three of the FA chemicals dominated this time period. The FA chemical choices misidentified were from chemicals with similar spectra. FIGS. 4A-4C show the spectral fit plots for the three most common chemicals, Chemical 4, Chemical 2, and Chemical 1 from FIG. 3, respectively.

In FIGS. 4A-4C the line indicated with triangles gives the super-pixel spectrum for the false alarm region, the line indicated with squares is the chemical fit, and the line indicated with diamonds is the residual. Comparing the three super-pixel spectrum lines shows that the spectrum of the anomaly is similar in all cases. Small variations, such as the strength of the weak peak at about 11 microns, influence which of the chemical spectra is a best fit. None of these spectra is a good fit for the anomaly, so increasing the threshold in the identification step would remove this false alarm. However, raising the threshold reduces the sensitivity to real gas plumes, so it would be better to have a more specific means of removing these false alarms.

Visualization of the Spectral Distribution of False Alarms

As has been previously discussed, one false alarm can have multiple identities, even though the underlying spectrum of the false alarm changes only slightly over the course of several days. This suggests that underlying sources of false alarms have signatures that might be recognized, even though the false identity may bounce between a number of similar chemical spectra.

An instructive visualization of the problem can be created by studying a scene with no gas, and plotting a PFA histogram from the data. For example, if a hyperspectral imaging instrument observed a relatively uncluttered scene for six hours with no gas releases in the scene, every detection would be by definition a false alarm.

Figure 6:
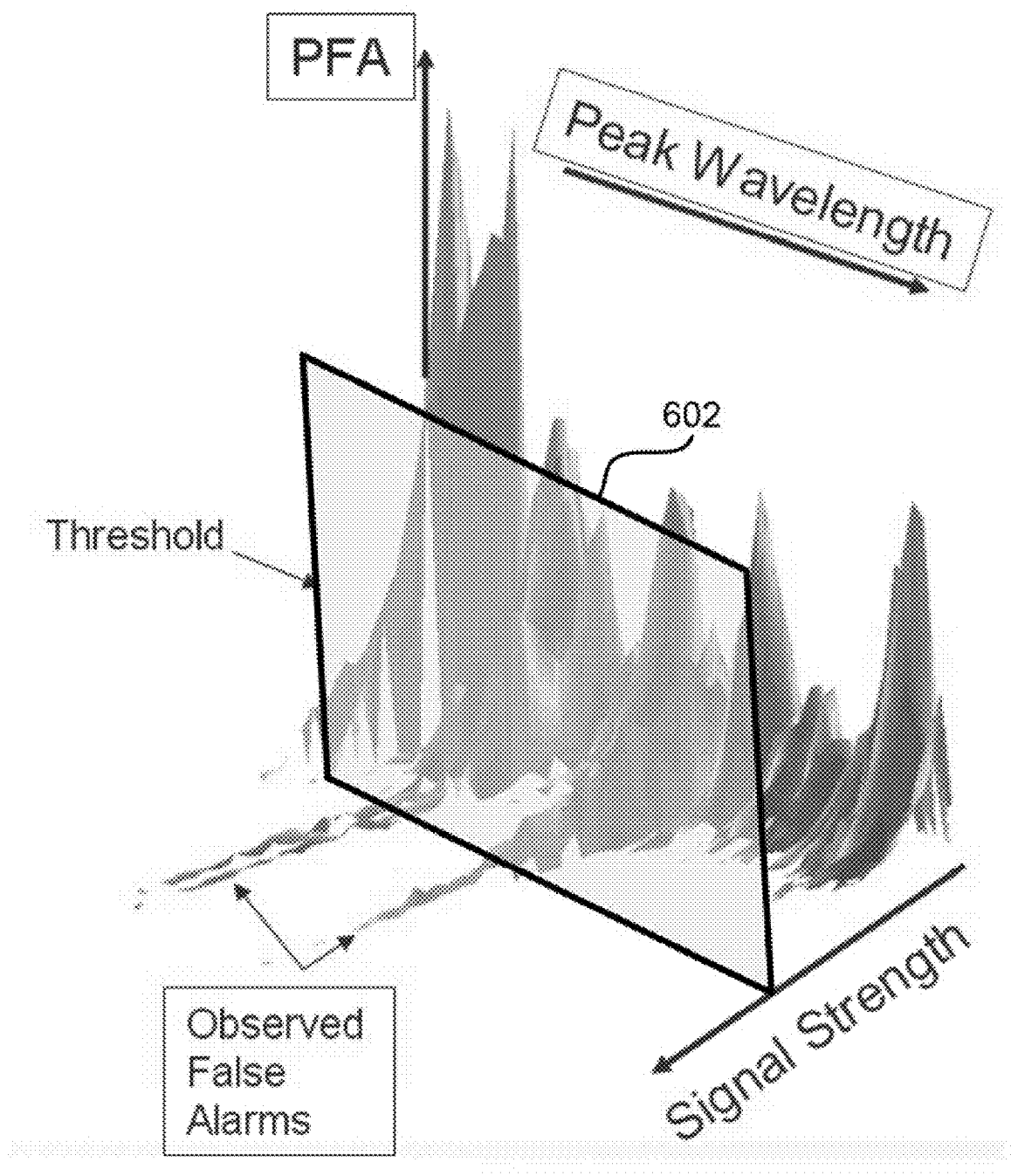
FIG. 6 shows a visualization of the false alarm spectral distribution for a collection of hyperspectral data sets.

FIG. 6 shows an illustrative histogram of the frequency of occurrence of false alarms during an exemplary observation of an uncluttered scene. The wavelength of the strongest spectral peak is used as one axis, while the quality of spectral fit (F statistic) is used as the signal strength parameter. PFA was calculated by simply dividing the number of false alarms by the number of data cubes.

FIG. 6 shows two clusters of strong false alarms, which correlate to anomalies in the exemplary scene. The exemplary scene included several hot metal objects and a layer of rock in the background (believed to be limestone with a strong carbonate feature), and these background anomalies generated false alarms that greatly exceeded that of the remainder of the spectral region. False alarm identities are likely to be dominated by chemicals that happen to have strong absorption features in either of these two areas. The remainder of the spectral terrain should be relatively free of false alarms.

Normally a uniform threshold is applied, such as a minimum F statistic, to suppress false alarms, which is suggested by the transparent plane 602 in FIG. 6. False alarms with strong spectral fits end up exceeding the threshold 602, so these end up retained as false alarms in the exploited output. FIG. 6 suggests that applying a constant threshold is not only allowing some false alarms to pass through, but is also giving up sensitivity in other areas. Most of the false alarm surface is well below the threshold, so presumably a lower threshold could be applied if the strong false alarms could be suppressed.

Another way of looking at FIG. 6 is to suggest that in this scene, the instrument has a lower sensitivity for chemicals in two narrow spectral regions, as the scene itself generates signatures in these regions. This logic is correct if it is assumed that operation of the instrument at a limiting false alarm rate is desired, and no other filters are applied.

Scene-Specific PFA Estimates

FIG. 6 provides a visualization of the PFA distribution for a specific scene. To make this information useful in estimating the PFA for individual chemicals leads to a form of the data that is easily processed as part of the exploitation process. The transformation may follow these steps, according to one embodiment:

1) A subset of the available data for the scene that is believed to contain no gas is isolated. The selection can be done using outside knowledge (plant is shutdown, workers are opening machinery, no heat is emanating from equipment, etc.) or by preprocessing the data once to highlight periods of inactivity.
2) The no-gas data is processed with the full gas library using a low or very low threshold to generate a maximum number of false alarms. The spectral fit statistic is retained for each false alarm.
3) A cumulative histogram is created in the form shown in FIG. 5. The histogram accumulates false alarms by chemical, summing in decreasing order of fit statistic. Each histogram gives an estimate of the PFA for any subsequent detection of a chemical, based on the fit statistic measure for each "hit."
4) The raw histogram is curve fit to provide for easy interpolation of the PFA for any given fit statistic. In one approach, the Gaussian error function (erfc) may be used as a basis for the curve fit, using the three fit coefficients (fa0, fa1, fa2) in the following form, where fFvalue is the fit coefficient for the super pixel spectrum being tested:

if (fFvalue>fa2)
{
fPFA=fa0*erfc(fa1*(fFvalue−fa2));
}
else
{
fPFA=1−(fa0*erfc(fa1*(fa2−fFvalue)));
}

Figure 5:
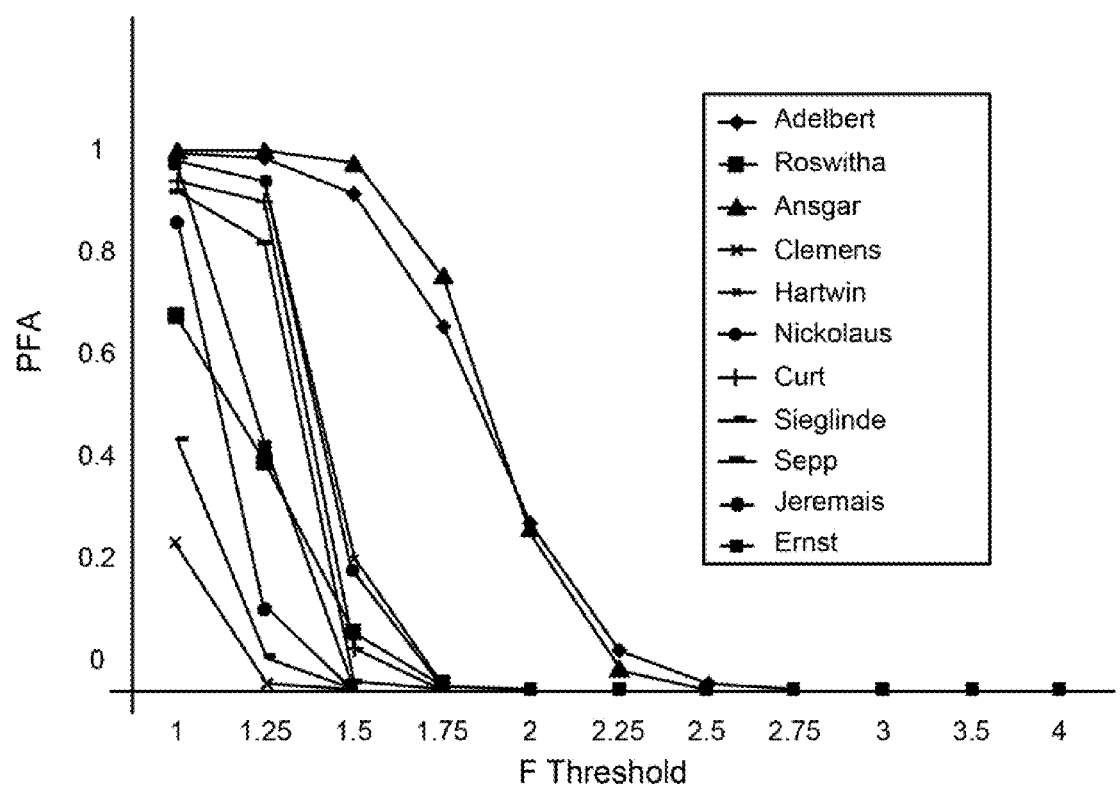
FIG. 5 is a histogram of several chemical gases according to one embodiment.

A typical smoothed output result from this formula is shown in FIG. 5.

The histogram shown in FIG. 5 was derived from data collected from a scene with no gas present. In this case, the two strong false alarms were routinely identified as Adelbert and Roswitha, respectively (Adelbert was selected on the carbonate feature). If a typical 1.75 threshold is applied on the X-axis in FIG. 5, a high probability of getting a false alarm would be expected on both of these chemicals, and a low probability of getting any other false alarm. However, if a Roswitha plume was observed with a fit statistic of 3.0 or higher, it would be convincing that it really was the chemical and not the false alarm, as the Roswitha PFA falls to near zero at a fit statistic of 2.5.

The implications of FIG. 5 are that for every chemical in the library, there is a statistical "gray area" where there is uncertainty as to whether a material is a plume or false alarm. Very strong plumes with high fit statistics are never in question, but as the plumes become weaker, the PFA increases.

Also note that as much as half of the spectral library may never show up as a false alarm in extended examinations of PFA. All of the spectra in the library compete to explain false alarms, so many of the spectra are never selected because others are always better fits. For example, it is extremely unlikely to have a false alarm that resembles a complex and unique spectrum such as ammonia, so ammonia generally ends up with a PFA of zero regardless of the fit statistic.

Statistical Filtering

Given a set of PFA curves for every chemical in the identification library (FIG. 5), estimations of the PFA for every chemical that is identified may be made. This is done on a plume-by-plume basis, as each potential plume has a different fit statistic. An obvious use of these PFA estimates is to remove results that have high PFA, so that results that are unlikely to be false alarms are left. This is not a perfect filter, as exact knowledge of whether a specific result is or is not a false alarm is not available. However, statistical filtering can be very useful.

Figure 7A:
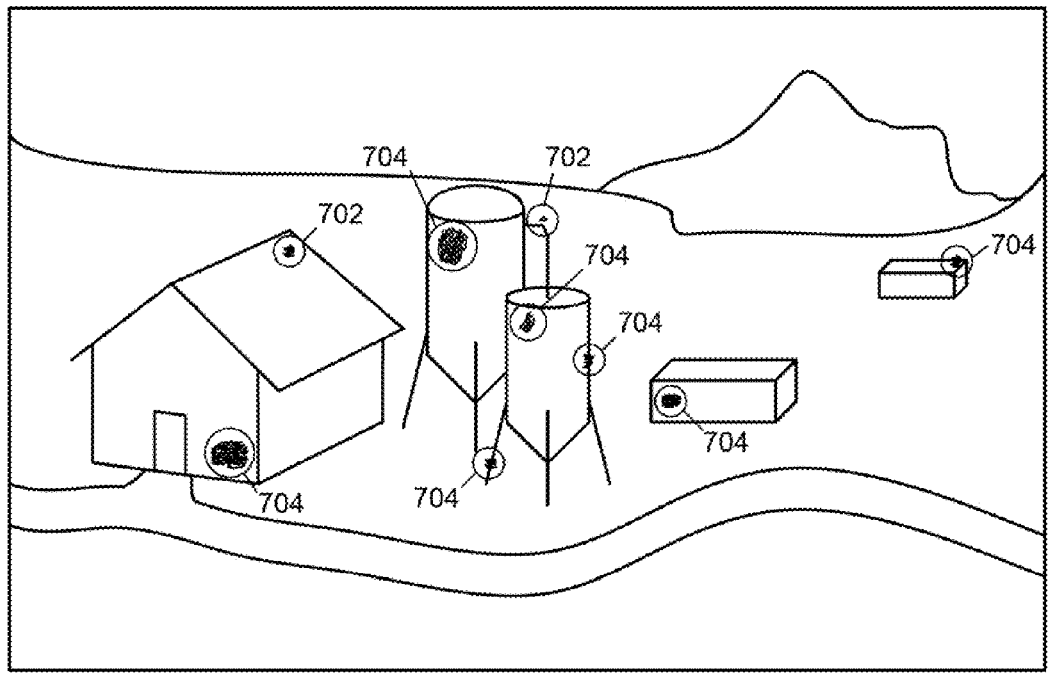
FIG. 7A shows a simplified rendering of a hyperspectral image which is consistent with images produced with a low detection threshold and no PFA filtering, according to one embodiment.
Figure 7B:
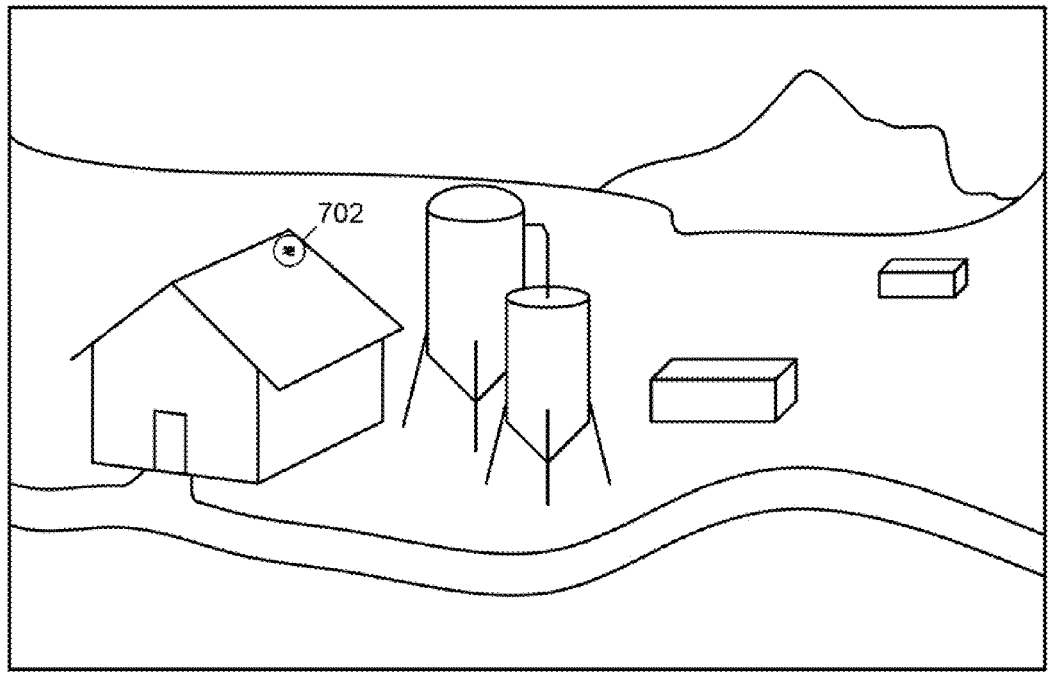
FIG. 7B shows a simplified rendering of a thermal image which is consistent with images produced with a low detection threshold and PFA filtering applied, according to one embodiment.

A good example of the impact of statistical filtering can be seen in FIGS. 7A and 7B. In FIG. 7A, all identifications 702, 704 of a gas are shown, superimposed on the same background image. Some of the locations are actual releases of the gas 702, while the remainder are false alarms 704. In FIG. 7B, a 1% maximum PFA may be applied, using false alarm data derived from a previous day's no-gas data. Only a small portion of the gas identifications may pass the 1% PFA filter. It can be seen that the PFA filter did a good job of removing false alarms. However, some small portions of the "real" gas plume were also eliminated, because their fit statistics were too low.

Figure 8A:
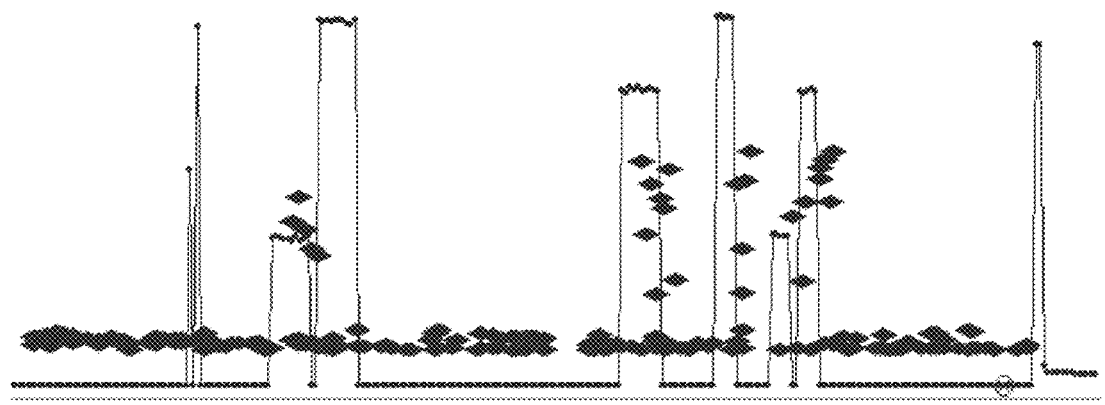
FIG. 8A shows a timeline view of unfiltered gas detections, according to one embodiment.
Figure 8B:
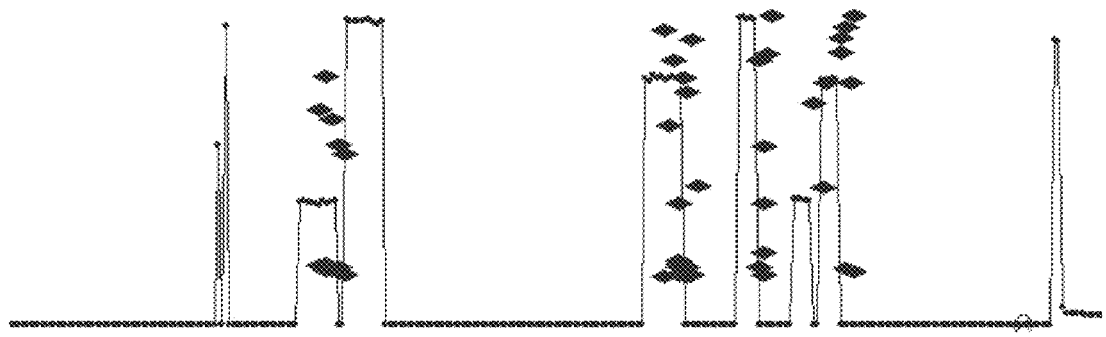
FIG. 8B shows a timeline view of filtered gas detections using a 1% maximum PFA filter, according to one embodiment.

Although FIGS. 8A and 8B show the utility of statistical filtering, the example is not a particularly difficult case. FIG. 8A shows the timeline view of unfiltered gas detections, which are indicated as diamonds. The gas flow rate is shown as the line. FIG. 8B shows the gas detections after applying a 1% maximum PFA filter. The gas mass flow rates were high enough that simply raising the fit statistic threshold would have eliminated the false alarms, although the weaker plumes (bottom diamonds on FIG. 8B) would also have been eliminated. Statistical PFA filtering is of much more utility when the gas rates are low and there is no clear separation between the false alarm population and actual gas plumes. These situations are described in more detail below.

Statistical PFA Filtering at Low Gas Rates

Statistical PFA filtering may perform better than raising the fit statistic when gas rates are so low as to be only marginally detectable. Referring again to FIGS. 1A and 1B, FIG. 1A shows a timeline of false alarms and gas detections before statistical filtering. Although actual gas detections are mixed in with the results, the strong false alarms make the actual gas plumes difficult to find without some other level of filtering.

FIG. 1B shows the same data after applying a 1% maximum PFA filter. The majority of the false alarms are stripped away, exposing the most likely actual gas plumes. In this case, it was known which types of gases were being released. Both chemical Eckhard and Lorenz were correctly identified, resulting in a total of 10 correct identifications. One residual false alarm remains, highlighted as item 102 on FIG. 1B. This remaining false alarm 102 is obscured beneath the larger plume super pixel in FIG. 1A, and is therefore not visible.

Figure 9A:
FIG. 9A is a timeline with a lower threshold before filtering according to one embodiment.

Referring again to FIGS. 1A and 1B, these figures reflect filtering performed on a conventional exploitation with a normal F statistic threshold (F=1.75), according to one embodiment. The statistical PFA filter can be leveraged by rerunning the same data with a lower F statistic threshold (F=1.25). This will generate many more false alarms, but should provide additional sensitivity to weaker gas plumes. FIG. 9A shows a typical image run at the lower threshold (F=1.25). False alarms now dominate the scene. The timeline view in FIG. 9A shows that these false alarms are continuous, completely hiding any underlying gas data. Of course, the PFA filter has not yet been applied.

Figure 9B:
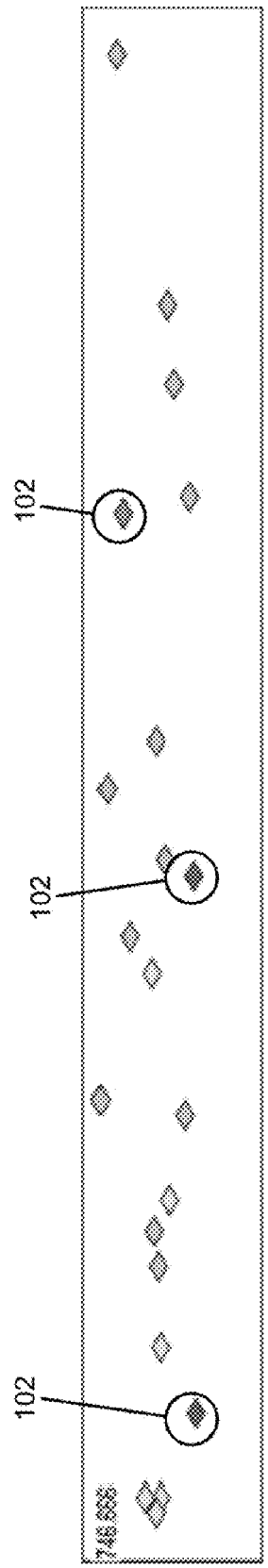
FIG. 9B is a timeline with a lower threshold after a 1% maximum PFA filter is applied according to one embodiment.

The high false alarm rate in the unfiltered FIG. 9A data makes it difficult to find the times when an actual gas plume was identified. However, the low threshold data can be filtered to remove likely false alarms. The result of applying the PFA filter is shown in FIG. 9B. This time the number of correct gas identifications has increased from 10 to 18 occurrences (when comparing FIGS. 1B and 9B), while the number of residual false alarms 102 has gone from one to three (when comparing FIGS. 1B and 9B). In other words, lowering the threshold before PFA filtering results in increased sensitivity, but also introduces a few more false alarms.

Figure 10A:
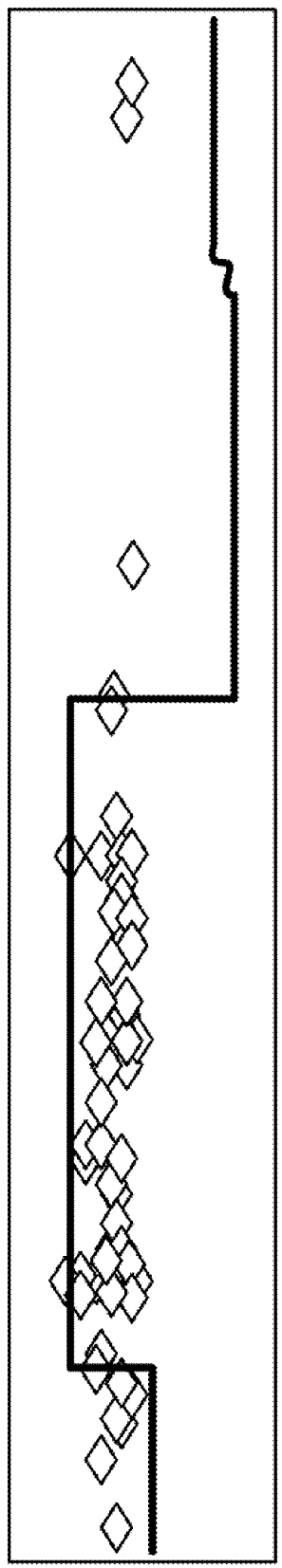
FIG. 10A is a gas flow timeline including unfiltered detections according to one embodiment.
Figure 10B:
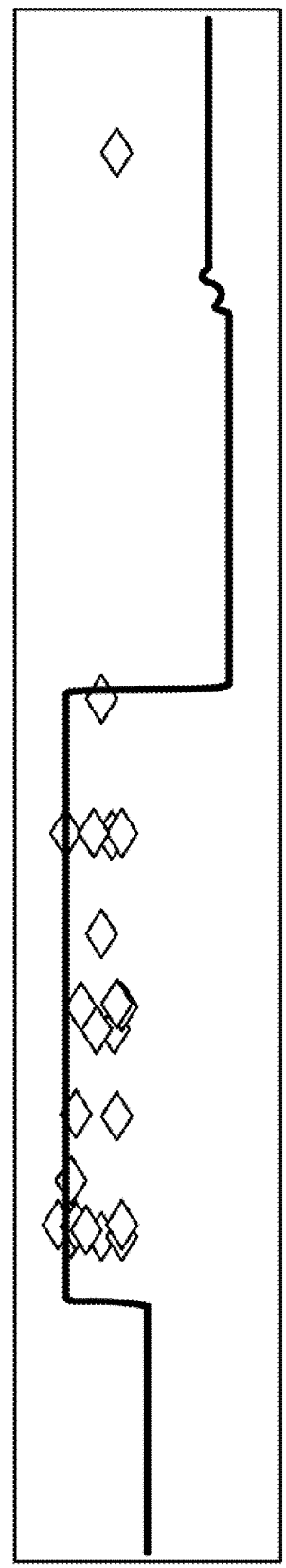
FIG. 10B is a gas flow timeline including filtered (1% maximum PFA) detections according to one embodiment.

The data sets shown in FIGS. 1A, 1B, 9A, and 9B were taken during controlled gas releases, so the detection history can be compared to the actual gas rate. Also, any system allowing filtering by PFA can be used to look at single gas identities to obtain more detail about the impact of statistical filtering. FIG. 10A shows just the gas Lorenz identifications from the low threshold run without PFA filtering. This is the same data set as shown in FIG. 9A, but only Lorenz data is shown. FIG. 10B shows the same Lorenz data, but identifications with a PFA over 1% have been suppressed.

Comparing FIGS. 10A and 10B shows the impact of statistical filtering. A 1% PFA filter removes the lower confidence plumes, particularly at the beginning of this sequence. False identifications, such as those toward the end of the sequence, are also suppressed.

Figure 11A:
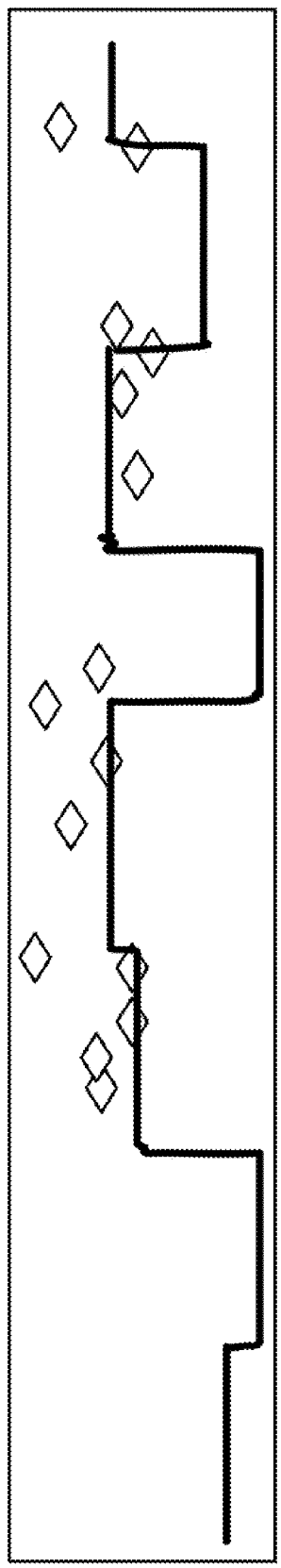
FIG. 11A is a gas flow timeline including unfiltered detections according to one embodiment.
Figure 11B:
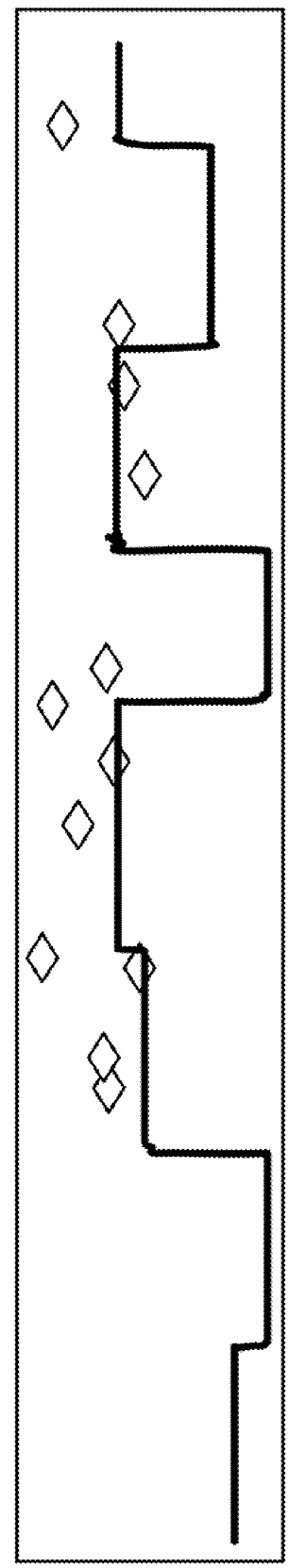
FIG. 11B is a gas flow timeline including filtered (1% maximum PFA) detections according to one embodiment.

FIGS. 11A and 11B repeat the comparison, but with a much more spectrally unique gas, specifically Eckhard. In this case, there is only a small reduction in the number of identifications when the 1% PFA filter is applied. Gas identifications which are of spectrally unique gases are unlikely to be false alarms, and are therefore not strongly affected by PFA filtering.

FIGS. 10A-11B show the impact of statistical filtering from the point of view of an analyst evaluating a day's worth of data. A more quantitative estimate of the benefits of filtering can be obtained using receiver operating characteristic (ROC) curves.

Measuring Filter Performance with Roc Curves

The tradeoffs between probability of detection (PD) and PFA outlined previously are typical of any filtering system. In general, it is best to shown both PD and PFA on the same plot, so that differences in filter performance can be distinguished from simple differences in threshold settings. The most common way to do this is with receiver operating characteristic curves, commonly referred to as ROC curves.

Classical ROC curves deal with the binary situation where a detection either does or does not occur, and the result can be either true or false. Hyperspectral data has the added complexity that with large gas libraries, there are hundreds of different ways to be wrong, but only one way to be right (the released gas is identified). One way to deal with this is to show cumulative ROC curves. The cumulative PFA is the sum of the probability of false alarm for all of the chemicals in the library, counting each chemical no more than once per data cube.

Figure 12:
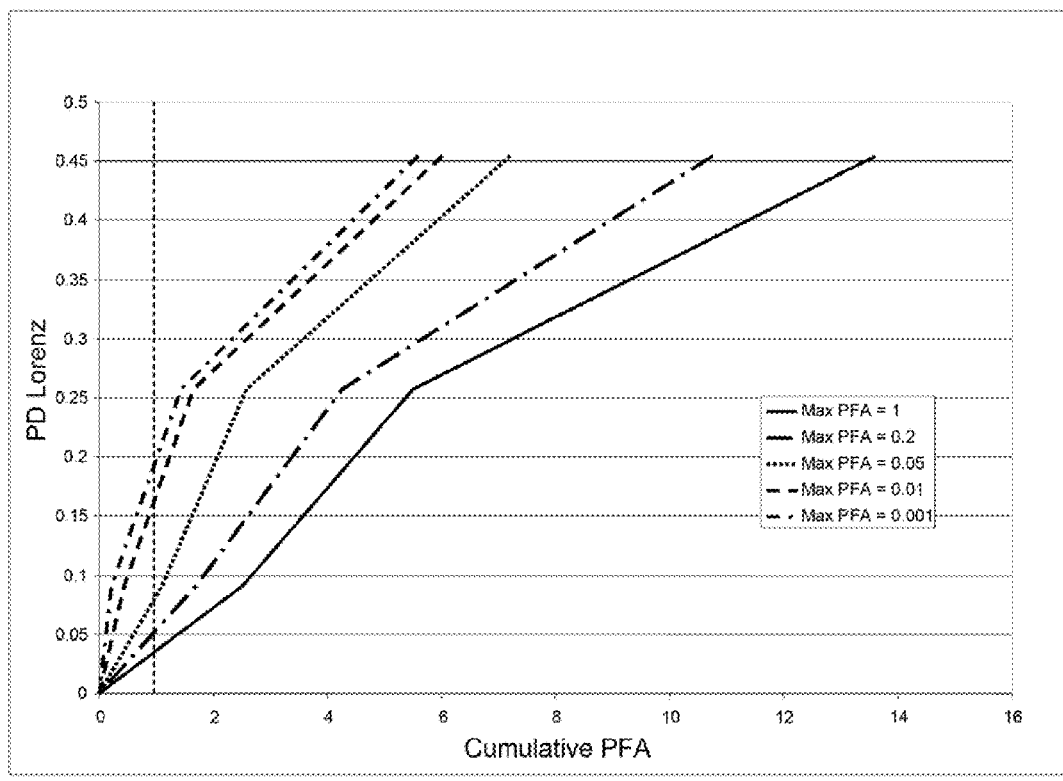
FIG. 12 shows a cumulative ROC curve for a gas according to one embodiment.

FIG. 12 shows a cumulative ROC curve for the Lorenz data shown in FIGS. 10A-11B. For simplicity, all Lorenz data cubes were treated together, including the very low gas rate data where Lorenz was seldom detected. The PD is therefore low in all cases. PD can be estimated independently of PFA.

The dashed line in FIG. 12 is set at a cumulative PFA of 1, which means that it can be expected that an average of one false alarm per data cube will be detected, where the false alarm may be any of the chemicals in the identification library. It is interesting that the PD for Lorenz continues to improve as the PFA limit is reduced to every very low levels. Of course, a PD maximum of zero would guarantee zero identifications, so this concept cannot be carried to extremes. Comparing the unfiltered bottom line (max PFA=1.0) to the top line (max PFA=0.001) shows a factor of five improvement in PD at the set false alarm rate.

Figure 13:
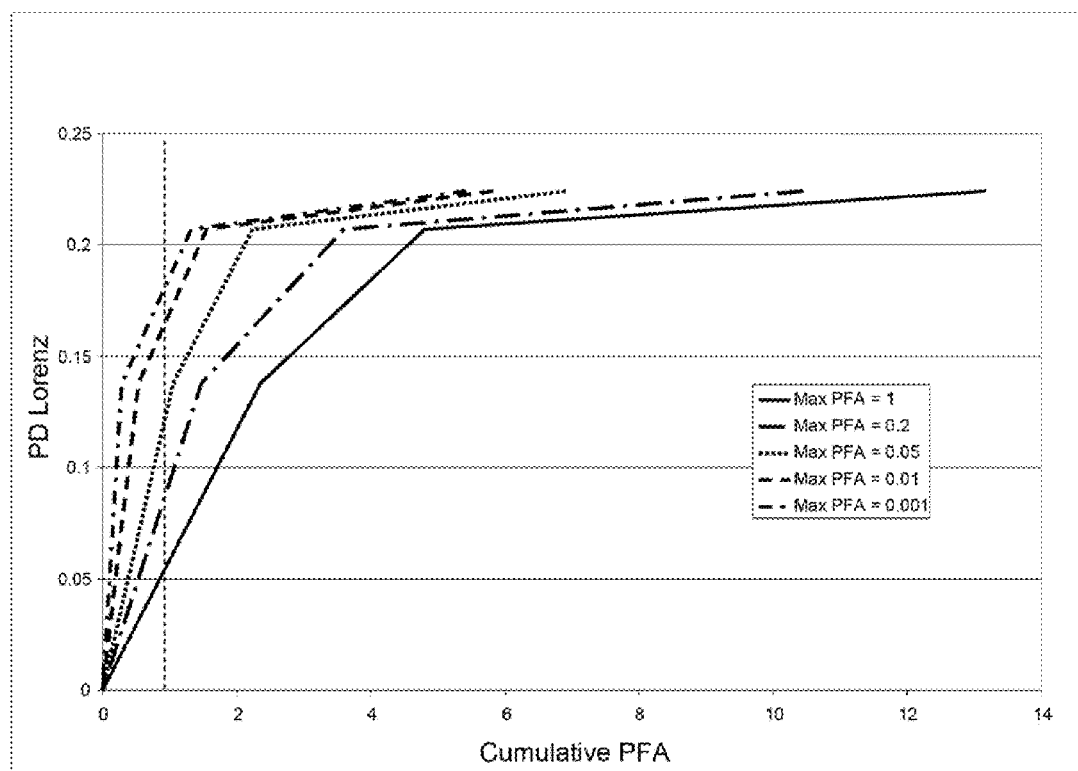
FIG. 13 shows a cumulative ROC curve for a gas according to one embodiment.

FIG. 13 shows a similar cumulative ROC curve for gas Eckhard. Again, application of the filter improves the PD by about a factor of 5 if a maximum cumulative PFA of 1 false alarm per cube is set. Note that the benefit of filtering falls off to almost zero if higher false alarm rates are tolerable. False alarm filtering is of no value if false alarms can be tolerated.

The ROC curves in FIGS. 12 and 13 reflect the performance of a completely automated set of filters. The improvement in PD due to filtering does not mean that application of a PFA filter increases the sensitivity of the system by a factor of five compared with a human analyst. Human analysts provide excellent filters, and would likely equal or exceed the performance of an automated filter, if they were given enough time.

Working with Small Truth Datasets

The examples shown so far have taken advantage of situations where there is a large body of data representing the no-gas condition. This situation may occur if persistent monitoring is undertaken, typically with a ground-based sensor. Even with a persistent sensor, it takes time to accumulate background data to create a comprehensive statistical model of the background. It is desirable to be able to generate reasonable estimates of the PFA distribution using small numbers of no-gas data cubes. In the limit, it would be ideal to be able to make PFA estimates using only one starting cube.

The obvious problem working with one no-gas data cube is that false alarm identities change over time. FIG. 3 showed an extreme case of one false alarm taking on eight identities over a period of two days, but alternation between several identities is common. If any data cube is selected at random from the population shown in FIG. 3, only one of the eight false alarms represented will be arrived at. The other seven possible false alarms would not appear in an attempt at a PFA distribution unless they happened to also be selected for one of the other persistent false alarms in the scene.

Although it is not possible to perfectly estimate the global population statistics for all false alarms from a small set of no-gas cubes, it is possible to do much better than to take the small set of observed false alarms as the limit of knowledge. The key to an improved estimate follows from two observations:

1. Although the identities of false alarms change over time, the underlying super-pixel spectra for the anomaly being identified change very little. The different false identities all tend to be from chemicals that have similar spectra, and compete to identify the false alarm.

2. The most likely identities to be selected for any given false alarm will always be listed as "close seconds" during the identification step.

Item 1 has already been described with reference to FIGS. 4A-4C, as an example. The idea that the application of random Gaussian noise to a limited number of no-gas files could produce the richness of statistics to satisfy operational needs has also been explored. Although this approach was successful, it is computationally burdensome. Using the "close seconds" approach takes advantage of calculations that are inevitably done with the initial exploitation of the data.

Item 2 takes into account how each false alarm obtains an identity. During the exploitation process, each possible gas plume is a clump of connected pixels (a super-pixel) that is combined to generate an average spectrum. This average spectrum is compared against all of the chemicals in the identification library to find a fit. (In practice, the comparison is one using a whitening transform to suppress background features, but this detail can be ignored for now.)

Given that the super-pixel spectrum is being compared to every chemical in the library, there is bound to be a best fit. There is also inevitably a second best, third best, and so on down the list of chemicals. The identification process produces a rank ordering of how well every chemical in the library fits the particular false alarm. If there are a number of chemicals with very close fit statistics, these "runners up" are likely to show up at some later point as the identity of the false alarm.

As an example, consider the several strong false alarms that resulted from hot metal surfaces, as described in previous examples. In one such example, over the course of several hours, this same location took on three false alarm identities, as shown in TABLE 1.

TABLE 1

| False Alarm identities over a period of several hours | |
|---|---|
| False ID Chemical Name | Frequency of Occurrence |
| Lambert | 67% |
| Hans | 31% |
| Armin | 3% |

If a data cube is randomly selected from this set, the most likely situation is that one will be chosen with the false alarm identified as Lambert, but it might also be one of the other two chemicals. TABLE 2 shows the fit statistics for one example data cube, showing not only the best fit chemical (Lambert) but also the other chemicals that were near the top of the list.

TABLE 2

| Alternate chemical identities for false alarms (Lambert) | | | |
|---|---|---|---|
| Rank | False ID Chemical Name | Fit Statistic | Ratio to First |
| 1 | Lambert | 1.8649 | 1.000 |
| 2 | Hans | 1.8649 | 1.000 |
| 3 | Gisa | 1.7990 | 0.965 |
| 4 | Armin | 1.7270 | 0.926 |
| 5 | Roswitha | 1.7060 | 0.915 |
| 6 | Carina | 1.6725 | 0.897 |
| 7 | Rudi | 1.6214 | 0.869 |

In TABLE 2 it is clear that for this cube it was about equal as to whether chemical Lambert or chemical Hans was selected to identify the false alarm. Both had the same fit statistic out to four decimals (the difference occurred in the sixth decimal.) Also note that gas Armin shows up as an alternative, but with a significantly lower fit statistic. Recall from TABLE 1 that gas Armin did show up during this data collect, but only 3% of the time. From TABLE 2 it would be expected that gas Gisa would also show up on occasion, but less often than Lambert or Hans. Gisa did not occur after 3½ hours of data, but it might well have shown up if the data collection had continued for longer.

TABLE 3 shows another example from the same data set. In this case chemical Hans was selected, but Lambert was a close second. Chemical Armin again shows up, this time in third place. These same common false alarms show up at the top of the list for all of the false alarm identifications for this one false alarm region, although the exact ordering differs from case to case.

TABLE 3

| Alternate chemical identities for false alarms (Hans) | | | |
|---|---|---|---|
| Rank | False ID Chemical Name | Fit Statistic | Ratio to First |
| 1 | Hans | 2.0181 | 1.000 |
| 2 | Lambert | 1.9091 | 0.946 |
| 3 | Armin | 1.7409 | 0.863 |
| 4 | Gisa | 1.7053 | 0.845 |
| 5 | Roswitha | 1.7025 | 0.844 |
| 6 | Carina | 1.6166 | 0.801 |
| 7 | Rudi | 1.6120 | 0.799 |

The relationship between close spectral identities and the probability of false alarm can be used to improve the estimates of the global false alarm distribution when only a small number of no-gas data cubes are available. It is helpful to consider the limiting case where only one no-gas data cube is available to work with.

Consider the case where a false alarm in a single no-gas data cube has two chemicals with exactly the same fit statistic, such as the case of Hans and Lambert in TABLE 2. Either of these chemicals is equally likely to be selected as a false alarm. Therefore, the PFA for Hans and Lambert from this one anomaly are both 50%. The single observation is split into two PFA contributors.

Figure 14:
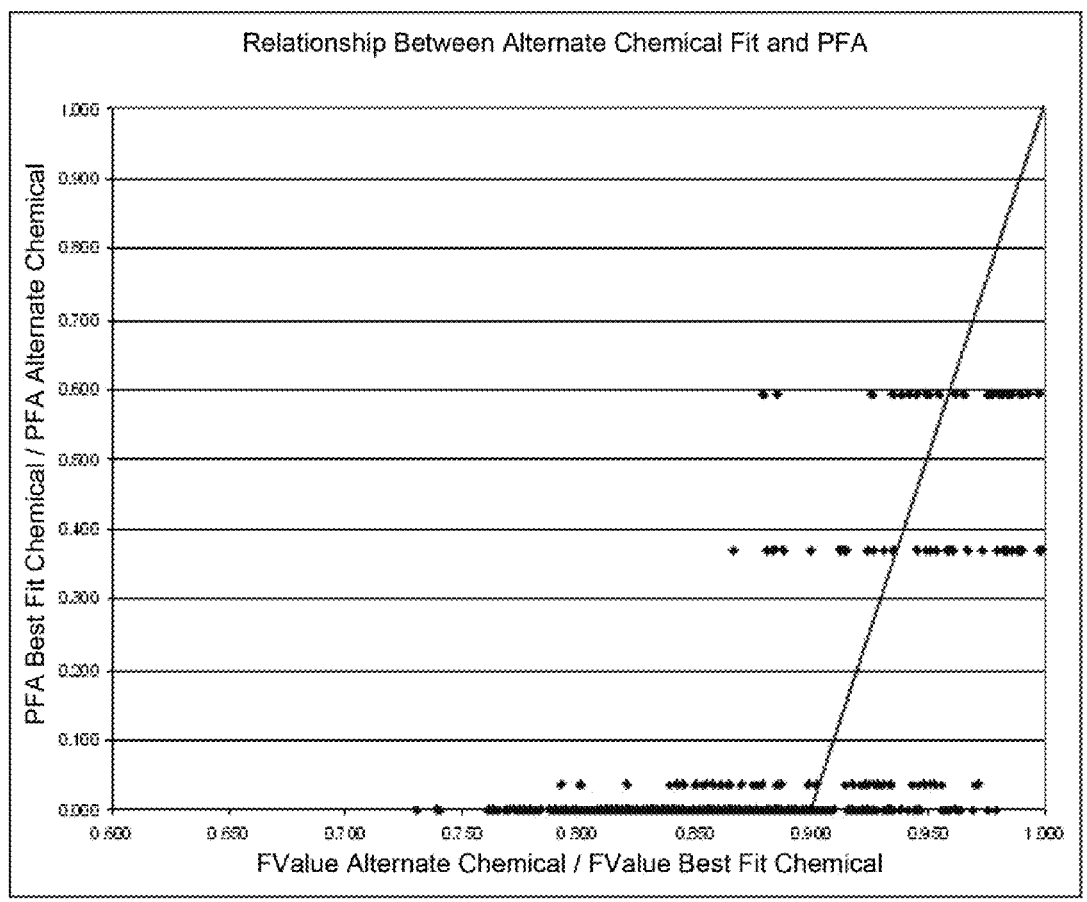
FIG. 14 shows a chart indicating the relationship between closeness of fit and frequency of occurrence for false alarm chemical gases.

This concept can be generalized to allow for weighting PFA contributions for cases where the competing spectra are similar, but not identical in fit statistic to the best fit chemical. FIG. 14 examines this relationship by comparing the closeness of fit statistics to the frequency the FA chemical occurred in the full population of data cubes. There is considerable scatter in this relationship, but it is clear that the likelihood of a competing chemical falls off rapidly as the fit statistic declines. Below about 90% of the best fit statistic, competing chemicals seldom appear.

A reasonable weighting of false alarm contributions can be made by using a linear weighting between the fit statistic ratio and the PFA. The weighting is 50/50 if the fit statistic ratio is 1.0 (e.g., both chemicals fit the false alarm spectrum equally well). The other end of the relationship can be anchored with a 0% weighting if the first statistic ratio is 0.9 or lower. TABLE 4 shows how this estimate is put into practice, for a single false alarm in a single data cube.

TABLE 4

Estimating the PFA contribution for chemicals other than best fit

| Chemical | Fit Statistic | Ratio to First | Weight | PFA Contribution |
|---|---|---|---|---|
| Hans | 2.0181 | 1.000 | 1.000 | 0.685 |
| Lambert | 1.9091 | 0.946 | 0.460 | 0.315 |
| Armin | 1.7409 | 0.863 | 0.000 | 0.000 |
| Gisa | 1.7053 | 0.845 | 0.000 | 0.000 |
| Roswitha | 1.7025 | 0.844 | 0.000 | 0.000 |
| Carina | 1.6166 | 0.801 | 0.000 | 0.000 |
| Rudi | 1.6120 | 0.799 | 0.000 | 0.000 |
| Totals | | | 1.460 | 1.000 |

Although by no means perfect, TABLE 4 shows that the two principal identities (Lambert and Hans) have been found for this location using just one data cube and given high PFAs. This process can be repeated with each false alarm, and with more data cubes as they become available. The quality of the estimate quickly improves as the number of sets of no-gas cubes approaches ten random samples. More no-gas data is always better, but diminishing returns set in quickly after this point.

As the set of no-gas data cubes becomes larger, the top false alarms tend to trade weighting back and forth, so there is little net effect. This is convenient, as switching PFA weighting computations is no longer done as the number of no-gas cubes becomes larger.

Note that this uncertainty as to the future identity of a false alarm closely resembles a similar problem where weak gas plumes are misidentified. Weak gas plumes are predictably misidentified as other chemicals with similar spectra. The probability of correct identification (PCI) can be estimated by comparing the fit statistic of the top two best fit chemicals from the library, where two chemicals with very similar fit statistics suggests a low confidence on the exact identity of the plume, according to one approach. False alarms have similar behavior, except that there is no "correct" identification.

Some operational complexity and additional record keeping is added to the process of data collection through the creation of at least some no-gas training data.

Figure 15:
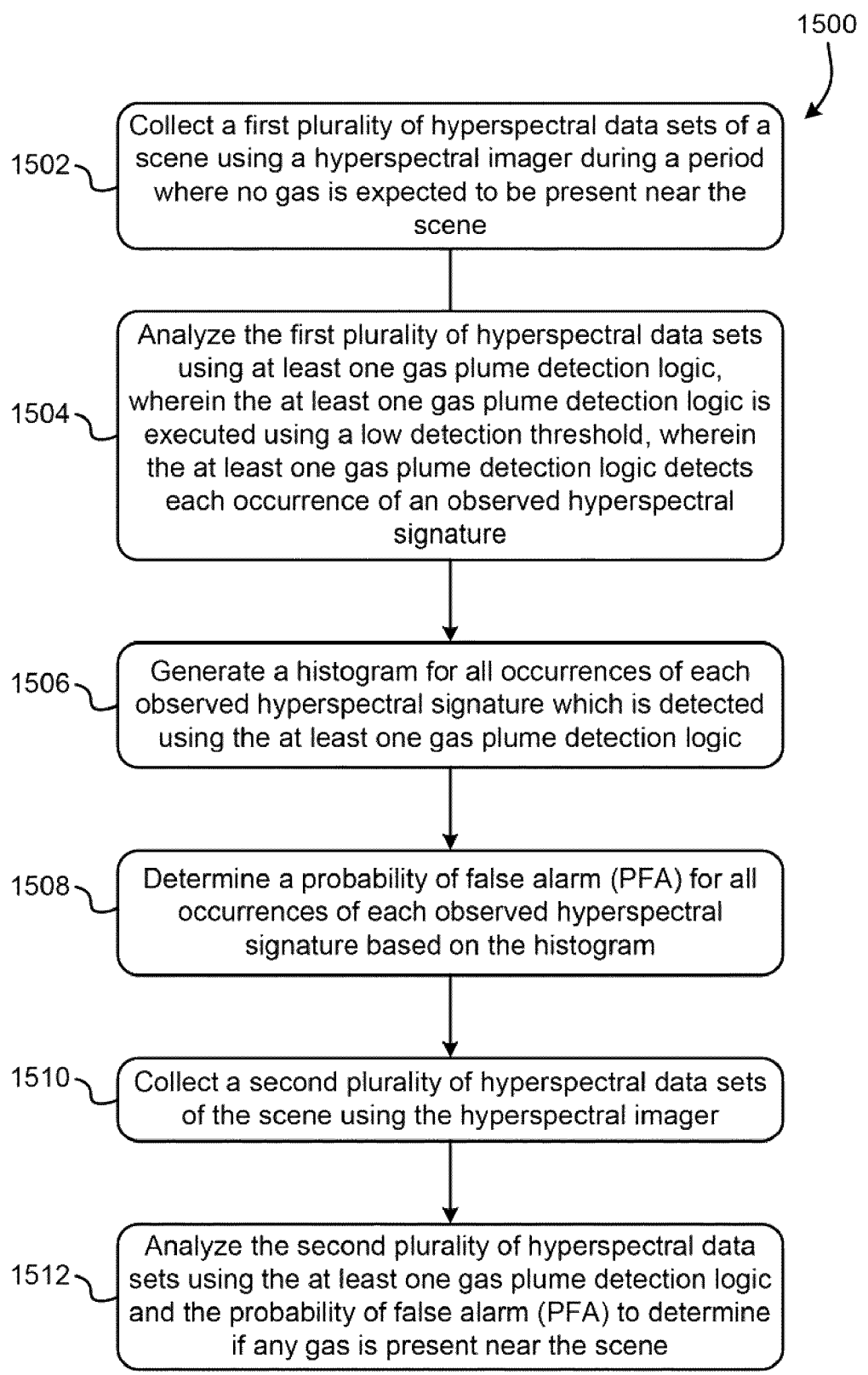
FIG. 15 is a flowchart of a method according to one embodiment.

Now referring to FIG. 15, a method 1500 for analyzing hyperspectral data is described according to one preferred embodiment. The method 1500 may be executed in any desired environment, and is not limited to the examples described herein.

In operation 1502, a first plurality of hyperspectral data sets of a scene is collected using a hyperspectral imager during a period where no gas is expected to be present near the scene. Any type of hyperspectral imager may be used to collect the data sets, such as a ground-based hyperspectral imaging (GBHSI) sensor, bolometric HSI sensors, airborne HSI sensors, etc.

According to some approaches, the period of data collection may be determined by knowledge that no gas is present during the recording times, and/or by best estimating, possibly through techniques previously described herein, such as when the plant is shutdown, when workers are opening machinery, when no heat is emanating from equipment, etc. Alternatively, the data may be preprocessed once to highlight periods of inactivity.

The scene may be described as any environment where gas identification is desired, such as a plant, reactor, processing facility, transportation devices and locations (such as a highway, street, train, airplane, ship, vessel, etc.), city, bunker, underground facility, water source (such as an ocean, river, lake, etc.), etc. Any environment where the presence and/or release of gas is desired to be identified without direct sampling of the gas is a candidate for a scene to be used with method 1500.

The first plurality of data sets may be described as a collection of hyperspectral images taken over a period of time for each of many wavelengths, preferably but not limited to the long-wave infrared (LWIR) spectrum, but may include any type of hyperspectral data sets.

In operation 1504, the first plurality of hyperspectral data sets is analyzed using at least one gas plume detection logic. The at least one gas plume detection logic is executed using a low detection threshold, and it detects each occurrence of an observed hyperspectral signature. There are many available gas plume detection logics and any one or more may be used to analyze the first plurality of hyperspectral data sets. How and to what degree the analysis on the first plurality of hyperspectral data sets takes place will depend on the gas plume detection logic or logics chosen.

The execution of the at least one gas plume detection logic at a low detection threshold indicates that many detections may be made. Included in these many detections of possible gases will undoubtedly be many false alarms, e.g., detections may be indicated as being a gas when in fact it is not the identified gas. Many objects in the background of the scene may cause these false alarms, along with gases having similar hyperspectral signatures as the misidentified gas. However, it is anticipated that many false alarms will be reported according to method 1500, as has been previously described.

In some approaches, analyzing the first plurality of hyperspectral data sets may further comprise comparing an observed hyperspectral signature from the plurality of first hyperspectral data sets to a library of known hyperspectral gas signatures. Any library of known hyperspectral gas signatures may be used for comparison purposes. In addition, in some approaches, a goodness-of-fit statistic may be calculated for the each occurrence of an observed hyperspectral signature against a signature of a known gas type from the library of known hyperspectral gas signatures. This goodness-of-fit statistic may be an F-statistic, or any other fit statistic as would be known to one of skill in the art. By using this method, a more accurate understanding of the similarities between he observed signature and the known gas signature may be achieved, thereby producing better results.

In operation 1506, a histogram is generated for all occurrences of each observed hyperspectral signature which is detected using the at least one gas plume detection logic. The generation of histograms has been described in greater detail previously herein, and is not duplicated here. However, it is noted that a histogram is generated for each type of gas according to the at least one gas plume detection logic's results. Also, in some approaches, the histogram may be arranged by an increasing goodness-of-fit statistic.

According to some preferred embodiments, the histogram may be generated with some additional steps. First, it may be determined if a signature of a known gas type from a library of known hyperspectral signatures is similar to an observed hyperspectral signature from the first plurality of hyperspectral data sets. Second, if there are any similar known signatures from the library, a histogram may be generated for that similar gas that is identical to the histogram generated for the similar observed hyperspectral signature. In this way, the transitory nature of false alarms, as described above, can be accounted for in the PFA calculations.

In operation 1508, a probability of false alarm (PFA) is determined for all occurrences of each observed hyperspectral signature based on the histogram. Determining a PFA has previously been described herein, and is not duplicated here. However, it is noted that for a gas signature which is included in a library of known gas signatures, but is not indicated as being detected by the at least one gas plume detection logic, a PFA of zero is assigned to that gas signature, since there were no false alarms indicated in the first set of hyperspectral data sets.

According to some approaches, determining a probability of false alarm (PFA) for all occurrences of each observed hyperspectral signature may comprise dividing a total number of occurrences of an observed hyperspectral signature by a total number of the first plurality of hyperspectral data sets collected. This results in a number in a range of zero to 1, wherein zero indicates that no false alarms were observed, and 1 indicates that all occurrences were false alarms.

In some approaches, the histogram may be modeled using a Gaussian error function to fit an observed relationship between the probability of false alarm (PFA) for all occurrences of each observed hyperspectral signature and a goodness-of-fit statistic. This results in a histogram for each observed signature that may resemble that shown in FIG. 5, which includes several signatures instead of just one.

In operation 1510, a second plurality of hyperspectral data sets of the scene are collected using the hyperspectral imager. The same or a different hyperspectral imager may be used to collect the second plurality of hyperspectral data sets of the scene; however, it is noted that a different hyperspectral imager may produce unanticipated differences in data collection behavior. Therefore, according to preferred embodiments, the same hyperspectral imager is used to collect the first and second plurality of hyperspectral data sets.

In operation 1512, the second plurality of hyperspectral data sets are analyzed using the at least one gas plume detection logic and the probability of false alarm (PFA) to determine if any gas is present near the scene. Whichever gas plume detection logic was used to analyze the first plurality of hyperspectral data sets is used to analyze the second plurality of hyperspectral data sets, since the differences introduced by using a different logic may be too cumbersome to overcome in determining the effect on PFAs.

According to some preferred approaches, the second plurality of hyperspectral data sets may be analyzed by detecting each occurrence of an observed hyperspectral signature in the second plurality of hyperspectral data sets, calculating a goodness-of-fit statistic for each occurrence of an observed hyperspectral signature from the second plurality of hyperspectral data sets against a signature of a known gas type from a library of known hyperspectral signatures, determining a probability of false alarm (PFA) at the goodness-of-fit statistic for the observed hyperspectral signature from the corresponding histogram, outputting a false alarm if the probability of false alarm (PFA) is equal to or above a preset threshold, and outputting an occurrence of the known gas type if the probability of false alarm (PFA) is below the preset threshold. By following this methodology, it can be determined if an occurrence of an observed signature in the second plurality of hyperspectral data sets is more likely to actually be the observed gas, or if it is more likely to be a false alarm. The threshold may be preset according to any desired level of damping. For example, if the threshold is preset to a PFA of 0.5, then a false alarm will be reported if it is more than likely (i.e., 50% or greater) that the observation is a false alarm, otherwise the occurrence will be reported as the detected gas type. In other embodiments, the threshold may be preset in a range of about 0.3 to about 0.7, such as 0.4, 0.6, etc. In some cases, the amount of false alarms indicated may justify increasing or decreasing the threshold.

Of course, the methods and techniques described herein may be implemented in a system and/or computer program product. A system may include a processor and a memory operatively coupled to the processor. The processor may receive a first plurality of hyperspectral data sets and a second plurality of hyperspectral data sets from a hyperspectral imager. The data sets may be processed or raw data, and may be received through any number of intermediary devices.

The description herein is presented to enable any person skilled in the art to make and use the invention and is provided in the context of particular applications of the invention and their requirements. Various modifications to the disclosed embodiments will be readily apparent to those skilled in the art and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

In particular, various embodiments of the invention discussed herein are implemented using the Internet as a means of communicating among a plurality of computer systems. One skilled in the art will recognize that the present invention is not limited to the use of the Internet as a communication medium and that alternative methods of the invention may accommodate the use of a private intranet, a Local Area Network (LAN), a Wide Area Network (WAN) or other means of communication. In addition, various combinations of wired, wireless (e.g., radio frequency) and optical communication links may be utilized.

The program environment in which one embodiment of the invention may be executed illustratively incorporates one or more general-purpose computers or special-purpose devices such hand-held computers. Details of such devices (e.g., processor, memory, data storage, input and output devices) are well known and are omitted for the sake of clarity.

It should also be understood that the techniques of the present invention might be implemented using a variety of technologies. For example, the methods described herein may be implemented in software running on a computer system, or implemented in hardware utilizing either a combination of microprocessors or other specially designed application specific integrated circuits, programmable logic devices, or various combinations thereof. In particular, methods described herein may be implemented by a series of computer-executable instructions residing on a storage medium such as a physical computer-readable medium. In addition, although specific embodiments of the invention may employ object-oriented software programming concepts, the invention is not so limited and is easily adapted to employ other forms of directing the operation of a computer.

The invention can also be provided in the form of a computer program product comprising a physical computer readable medium having computer code thereon. A computer readable medium can include any physical medium capable of storing computer code thereon for use by a computer, including optical media such as read only and writeable CD and DVD, magnetic memory, semiconductor memory (e.g., FLASH memory and other portable memory cards, etc.), etc.

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method for analyzing hyperspectral data, the method comprising:
    collecting a first plurality of hyperspectral data sets of a scene using a hyperspectral imager during a period where no gas is expected to be present in the scene;
    analyzing the first plurality of hyperspectral data sets using at least one gas plume detection logic, wherein the at least one gas plume detection logic is executed using detection threshold, wherein the at least one gas plume detection logic detects each occurrence of an observed hyperspectral signature;
    generating a histogram for all occurrences of each observed hyperspectral signature which is detected using the at least one gas plume detection logic;
    determining a probability of false alarm (PFA) for all occurrences of each observed hyperspectral signature based on the histogram;
    collecting a second plurality of hyperspectral data sets of the scene using the hyperspectral imager; and
    analyzing the second plurality of hyperspectral data sets using the at least one gas plume detection logic and the probability of false alarm (PFA) to determine if any gas is present in the scene.

2. The method of claim 1, wherein analyzing the first plurality of hyperspectral data sets further comprises comparing an observed hyperspectral signature from the plurality of first hyperspectral data sets to a library of known hyperspectral gas signatures.

3. The method of claim 2, further comprising calculating a goodness-of-fit statistic for the each occurrence of an observed hyperspectral signature against a signature of a known gas type from the library of known hyperspectral gas signatures.

4. The method of claim 3, further comprising arranging the histogram by an increasing goodness-of-fit statistic.

5. The method of claim 1, wherein determining a probability of false alarm (PFA) for all occurrences of each observed hyperspectral signature comprises dividing a total number of occurrences of an observed hyperspectral signature by a total number of the first plurality of hyperspectral data sets collected.

6. The method of claim 1, further comprising modeling the histogram using a Gaussian error function to fit an observed relationship between the probability of false alarm (PFA) for all occurrences of each observed hyperspectral signature and a goodness-of-fit statistic.

7. The method of claim 1, wherein generating a histogram for all occurrences of each observed hyperspectral signature further comprises:
    determining if a signature of a known gas type from a library of known hyperspectral signatures is similar to an observed hyperspectral signature from the first plurality of hyperspectral data sets; and
    generating a histogram for the known gas type which has a similar hyperspectral signature that is identical to the histogram generated for the similar observed hyperspectral signature.

8. The method of claim 1, wherein analyzing the second plurality of hyperspectral data sets using the at least one gas plume detection logic further comprises:
    detecting each occurrence of an observed hyperspectral signature in the second plurality of hyperspectral data sets;
    calculating a goodness-of-fit statistic for each occurrence of an observed hyperspectral signature from the second plurality of hyperspectral data sets against a signature of a known gas type from a library of known hyperspectral signatures;
    determining a probability of false alarm (PFA) at the goodness-of-fit statistic for the observed hyperspectral signature from the corresponding histogram;
    outputting a false alarm if the probability of false alarm (PFA) is equal to or above a preset threshold; and
    outputting an occurrence of the known gas type if the probability of false alarm (PFA) is below the preset threshold.

9. A system for detecting gas plumes, comprising:
    a processor; and
    a memory operatively coupled to the processor,
    wherein the processor receives a first plurality of hyperspectral data sets of a scene collected by a hyperspectral imager during a period where no gas is expected to be present in the scene,
    wherein the processor analyzes the first plurality of hyperspectral data sets using at least one gas plume detection logic which is executed using a detection threshold, wherein the at least one gas plume detection logic detects each occurrence of an observed hyperspectral signature,
    wherein the processor generates a histogram for all occurrences of each observed hyperspectral signature which is detected using the at least one gas plume detection logic,
    wherein the processor determines a probability of false alarm (PFA) for all occurrences of each observed hyperspectral signature based on the histogram,
    wherein the processor receives a second plurality of hyperspectral data sets of the scene using the hyperspectral imager, and
    wherein the processor analyzes the second plurality of hyperspectral data sets using the at least one gas plume detection logic and the probability of false alarm (PFA) to determine if any gas is present in the scene.

10. The system of claim 9, wherein the processor analyzes the first plurality of hyperspectral data sets by comparing an observed hyperspectral signature from the plurality of first hyperspectral data sets to a library of known hyperspectral gas signatures.

11. The system of claim 10, wherein the processor calculates a goodness-of-fit statistic for the each occurrence of an observed hyperspectral signature against a signature of a known gas type from the library of known hyperspectral gas signatures.

12. The system of claim 11, wherein the processor arranges the histogram by an increasing goodness-of-fit statistic.

13. The system of claim 9, wherein the processor determines a probability of false alarm (PFA) for all occurrences of each observed hyperspectral signature by dividing a total number of occurrences of an observed hyperspectral signature by a total number of the first plurality of hyperspectral data sets collected.

14. The system of claim 13, wherein the processor models the histogram using a Gaussian error function to fit an observed relationship between the probability of false alarm (PFA) for all occurrences of each observed hyperspectral signature and a goodness-of-fit statistic.

15. The system of claim 9, wherein the processor generates a histogram for all occurrences of each observed hyperspectral signature by:
   determining if a signature of a known gas type from a library of known hyperspectral signatures is similar to an observed hyperspectral signature from the first plurality of hyperspectral data sets; and
   generating a histogram for the known gas type which has a similar hyperspectral signature that is identical to the histogram generated for the similar observed hyperspectral signature.

16. The system of claim 9, wherein the processor analyzes the second plurality of hyperspectral data sets using the at least one gas plume detection logic by:
   detecting each occurrence of an observed hyperspectral signature in the second plurality of hyperspectral data sets;
   calculating a goodness-of-fit statistic for each occurrence of an observed hyperspectral signature from the second plurality of hyperspectral data sets against a signature of a known gas type from a library of known hyperspectral signatures;
   determining a probability of false alarm (PFA) at the goodness-of-fit statistic for the observed hyperspectral signature from the corresponding histogram;
   outputting a false alarm if the probability of false alarm (PFA) is equal to or above a preset threshold; and
   outputting an occurrence of the known gas type if the probability of false alarm (PFA) is below the preset threshold.

17. A computer program product embodied on a non-transitory computer readable medium, the computer program product comprising:
   computer readable code for receiving a first plurality of hyperspectral data sets of a scene from a hyperspectral imager collected during a period where no gas is expected to be present in the scene;
   computer readable code for analyzing the first plurality of hyperspectral data sets using at least one gas plume detection logic, wherein the at least one gas plume detection logic is executed using a detection threshold, wherein the at least one gas plume detection logic detects each occurrence of an observed hyperspectral signature;
   computer readable code for generating a histogram for all occurrences of each observed hyperspectral signature which is detected using the at least one gas plume detection logic;
   computer readable code for determining a probability of false alarm (PFA) for all occurrences of each observed hyperspectral signature based on the histogram;
   computer readable code for receiving a second plurality of hyperspectral data sets of the scene from the hyperspectral imager; and
   computer readable code for analyzing the second plurality of hyperspectral data sets using the at least one gas plume detection logic and the probability of false alarm (PFA) to determine if any gas is present in the scene.

18. The computer program product of claim 17, wherein the computer readable code for analyzing the second plurality of hyperspectral data sets using the at least one gas plume detection logic further comprises:
   computer readable code for detecting each occurrence of an observed hyperspectral signature in the second plurality of hyperspectral data sets;
   computer readable code for calculating a goodness-of-fit statistic for each occurrence of an observed hyperspectral signature from the second plurality of hyperspectral data sets against a signature of a known gas type from a library of known hyperspectral signatures;
   computer readable code for determining a probability of false alarm (PFA) at the goodness-of-fit statistic for the observed hyperspectral signature from the corresponding histogram;
   computer readable code for outputting a false alarm if the probability of false alarm (PFA) is equal to or above a preset threshold; and
   computer readable code for outputting an occurrence of the known gas type if the probability of false alarm (PFA) is below the preset threshold.

19. A method for analyzing hyperspectral data, the method comprising:
   collecting a first plurality of hyperspectral data sets of a scene using a hyperspectral imager during a period where no gas is expected to be present in the scene;
   analyzing the first plurality of hyperspectral data sets using at least one gas plume detection logic, wherein the at least one gas plume detection logic is executed using a detection threshold, wherein the at least one gas plume detection logic detects each occurrence of an observed hyperspectral signature;
   comparing an observed hyperspectral signature from the plurality of first hyperspectral data sets to a library of known hyperspectral gas signatures;
   calculating a goodness-of-fit statistic for the each occurrence of an observed hyperspectral signature against a signature of a known gas type from the library of known hyperspectral gas signatures;
   generating a histogram for all occurrences of each observed hyperspectral signature which is detected using the at least one gas plume detection logic;
   determining a probability of false alarm (PFA) for all occurrences of each observed hyperspectral signature based on the histogram;
   collecting a second plurality of hyperspectral data sets of the scene using the hyperspectral imager; and
   analyzing the second plurality of hyperspectral data sets comprising:
      detecting each occurrence of an observed hyperspectral signature in the second plurality of hyperspectral data sets;
      calculating a goodness-of-fit statistic for each occurrence of an observed hyperspectral signature from the second plurality of hyperspectral data sets against a signature of a known gas type from the library of known hyperspectral signatures;
      determining a probability of false alarm (PFA) at the goodness-of-fit statistic for the observed hyperspectral signature from the corresponding histogram;
      outputting a false alarm if the probability of false alarm (PFA) is equal to or above a preset threshold; and
      outputting an occurrence of the known gas type if the probability of false alarm (PFA) is below the preset threshold.

* * * * *